(12) United States Patent
Bellinzoni et al.

(10) Patent No.: US 10,041,103 B2
(45) Date of Patent: *Aug. 7, 2018

(54) HIGH THROUGHPUT QUANTIFICATION AND CHARACTERIZATION OF VIRUSES AND PRODUCTS THEREOF

(71) Applicant: BIOGÉNESIS BAGÓ URUGUAY S.A., Montevideo (UY)

(72) Inventors: Rodolfo Cesar Bellinzoni, Tigre (AR); Nicolás Magi, Escobar (AR); Emmanuel Gérard Etienne Régulier, Vicente López (AR); Ana Romo, Chascomús (AR); Marcelo Arnolfo Spitteler, San Martín (AR)

(73) Assignee: BIOGÉNESIS BAGÓ URUGUAY S.A. (UY)

(*) Notice: Subject to any disclaimer, the term of this patent is extended or adjusted under 35 U.S.C. 154(b) by 0 days.

This patent is subject to a terminal disclaimer.

(21) Appl. No.: 15/316,180

(22) PCT Filed: Jun. 5, 2015

(86) PCT No.: PCT/IB2015/054280
§ 371 (c)(1),
(2) Date: Dec. 5, 2016

(87) PCT Pub. No.: WO2015/186113
PCT Pub. Date: Dec. 10, 2015

(65) Prior Publication Data
US 2017/0198332 A1  Jul. 13, 2017

Related U.S. Application Data

(60) Provisional application No. 62/009,126, filed on Jun. 6, 2014.

(51) Int. Cl.
| | | |
|---|---|---|
| C12Q 1/06 | (2006.01) |
| C12Q 1/04 | (2006.01) |
| G01N 30/74 | (2006.01) |
| G01N 15/02 | (2006.01) |
| G01N 30/60 | (2006.01) |
| G01N 30/84 | (2006.01) |
| G01N 30/46 | (2006.01) |
| B01D 15/18 | (2006.01) |
| B01D 15/34 | (2006.01) |
| G01N 15/00 | (2006.01) |

(52) U.S. Cl.
CPC .......... C12Q 1/06 (2013.01); B01D 15/1885 (2013.01); B01D 15/34 (2013.01); C12Q 1/04 (2013.01); G01N 15/0205 (2013.01); G01N 30/468 (2013.01); G01N 30/6043 (2013.01); G01N 30/74 (2013.01); G01N 30/84 (2013.01); *G01N 2015/0065* (2013.01); *G01N 2030/8429* (2013.01); *G01N 2333/005* (2013.01)

(58) Field of Classification Search
None
See application file for complete search history.

(56) References Cited

U.S. PATENT DOCUMENTS

2008/0299545 A1  12/2008  Zhang et al.

FOREIGN PATENT DOCUMENTS

| AR | 085877 | 11/2013 |
|---|---|---|
| EP | 0190628 | 8/1986 |
| WO | 9207244 | 4/1992 |
| WO | 0138852 | 5/2001 |
| WO | 2004056456 | 7/2004 |
| WO | 2008109721 | 9/2008 |
| WO | 2009022174 A2 | 2/2009 |

OTHER PUBLICATIONS

Liebermann et al., Journal of Virological Methods vol. 50, Issues 1-3, Dec. 1994, pp. 281-291.*
Driskell et al., Analyst, vol. 136, pp. 3083-3090, 2011.*
Mar. 13, 2017 Office Action, U.S. Appl. No. 14/730,418.
Liebermann et al., 1994, Quantification of Adenovirus Particles, Journal of Virological Methods, 50, 281-292.
Barteling SJ et al., 1974, a simple method for the quantification of 140S particles of foot-and-mouth disease virus (FMDV). Arch Gesamte Virusforsch, 45(4) 362-364.
Barteling SJ., 1999, Need for further standardization of the 146- S test as the basis for final- Foot-and-Mouth Disease (FMD) Vaccine formulation, EUFMD Research Group Meeting, Appendix 17.
Spitteler MA et al., 2011, Foot and mouth disease (FMD) virus: Quantification of whole virus particles during the vaccine manufacturing process by size exclusion chromatography, Vaccine, 29, 7182-7187.

(Continued)

*Primary Examiner* — Shanon A. Foley
*Assistant Examiner* — Myron G Hill
(74) *Attorney, Agent, or Firm* — Law Offices of Albert Wai-Kit Chan, PLLC

(57) ABSTRACT

The present invention provides a high throughput method to quantify and characterize the size and integrity of viruses and viral molecules using chromatographic system and in-line Dynamic Light Scattering (DLS) technique. In one embodiment, the present method quantifies and characterizes the size and integrity of enveloped or non-enveloped virus, live or live-attenuated or inactivated virus, recombinant viral vectors, or virus-like particles (VLPs). In one embodiment, the present invention comprises a column-switching system for running multiple analyzes simultaneously. The present invention also provides a method to develop and evaluate virus containing products for the prevention of viral diseases. In another embodiment, the methods described herein serve as in-process quality control for manufacturing processes of virus vaccines.

12 Claims, 15 Drawing Sheets

(56) References Cited

OTHER PUBLICATIONS

Cartwright B et al., 1980, Serological and immunological relations between the 146S and 12S particles of foot-and-mouth disease virus. Journal of General Virology, 50, 369-375.

Doel TR et al., 1982, Comparative immunogenicity of 146S, 75S and 12S particles of foot-and-mouth disease virus, Archives of Virology, 73, 2, 185-191.

2008 Foot and mouth disease (ruminants) vaccine (inactivated) monograph 0063 Ph. Eur. Suppl. 6.0 Strasbourg, France. Council of Europe.

2009 The World Organization of Animal Health (OIE), Terrestrial Animal Health Code. Foot and mouth disease. vol. 1, Section 2.1.5.

Written Opinion, dated Aug. 25, 2015, for Biogénesis Bagó Uruguay S.A. et al., International Application No. PCT/IB2015/054280, filed Jun. 5, 2015.

International Search Report, dated Aug. 25, 2015, for Biogenésis Bagó Uruguay S.A. et al., International Application No. PCT/IB2014/054280, filed Jun. 5, 2015.

Cass R T et al., 2001, Rapid bioanaiysis of vancomycin in serum and urine by high-performance liquid chromatography tandem mass spectrometry using on-line sample extraction and parallel analytical columns, Rapid Commun. Mass Spectrom., 15, 406-412.

Grant RP et al., 2002, Generic serial and parallel on-line direct-injection using turbulent flow liquid chromatography/tandem mass spectrometry, Rapid Commun. Mass Spectrom., 16, 1785-1792.

Lago P. et al., 1993, A Quasi-Elastic Light-Scattering Detector for Chromatographic Analysis, Review of scientific instruments, 64(7), 1797-1802.

Citkowicz A., 2008, Characterization of virus-like particle assembly for DNA delivery using asymmetrical flow field-flow fractionation and light scattering, Analytical Biochemistry, 376 (2), 163-172.

Nov. 22, 2017 Office Action, U.S. Appl. No. 14/730,418.

\* cited by examiner

FMDV U.V. and DLS flow trace

% of FMDV concentrate
(by volume)

Figure 6C

BoHV-5 U.V. and DLS flow trace

−⊖− Viral concentration (μg/mL)
⋯•⋯ Particle size (nm)
−✱− Cell count (x10$^6$ cell/mL)

Time course of FMDV infection

HIGH THROUGHPUT QUANTIFICATION AND CHARACTERIZATION OF VIRUSES AND PRODUCTS THEREOF

CROSS-REFERENCE TO RELATED APPLICATIONS

This application is the National Stage of International Application No. PCT/IB2015/054280, filed Jun. 6, 2015, which claims the benefit of U.S. Ser. No. 62/009,126, filed Jun. 6, 2014. The entire contents and disclosures of the preceding applications are hereby incorporated by reference into this application.

Throughout this application, various publications are referenced. Disclosures of these publications in their entireties are hereby incorporated by reference into this application in order to more fully describe the state of the art to which this invention pertains.

FIELD OF THE INVENTION

The present invention relates to quantification and characterization of viruses, viral particles, virus-like particles (VLPs) and recombinant viral vectors. The present invention further pertains to development of products to prevent infectious diseases caused by enveloped or non-enveloped viruses and evaluation of products containing enveloped or non-enveloped viruses or virus-like particles. The present invention further pertains to development of products for gene therapy applications and evaluation of products containing recombinant viral vectors used in gene-therapy.

BACKGROUND OF THE INVENTION

Viruses are self-replicating entities that require either prokaryotic or eukaryotic cells in order to replicate and propagate. When a virus comes in contact with a susceptible cell at first it attaches itself to the cell and then enters it. Once inside the cell, the virus hijacks the protein synthesis machinery of the cell and commands it to manufacture the required components to assemble more copies of itself. After a certain amount of time, the virus copies exit the cell either bursting the cell open or budding through the cell membrane. Viruses are classified according to several taxonomic criteria, one of the most relevant being whether they either have or lack a phospholipid bilayer envelope.

Both enveloped and non-enveloped viruses are found among human and veterinary pathogens. One of the most important veterinary disease caused by a non-enveloped virus is Foot-and-Mouth Disease (FMD) caused by the Foot-and-Mouth Disease Virus (FMDV). Another example of a non-enveloped virus causing big impacts on livestock productivity is Bovine Rotavirus, the causative agent of neonatal diarrhoea in calves. Some examples of enveloped viruses causing veterinary diseases include Bovine Herpesviruses 1 and 5 (BoHV-1 or BHV-1 and BoHV-5 or BHV-5) which are the etiologic agents of Infectious Bovine Rhinotracheitis and Bovine Herpetic Encephalitis respectively; the Bovine Parainfluenza Virus 3 (PI3 o BPIV-3) associated with the bovine respiratory disease (BRD) complex; and the Rabies Virus which is the pathogen causative of lethal encephalitis in both animals and human beings.

FMD is a severe and highly contagious disease affecting cloven-hoofed animals, including cattle, swine, sheep, goats and deer. Foot-and-mouth disease symptoms include fever, blisters in the mouth and on the feet and teats, drop in milk production, loss of appetite and weight and lameness.

The disease is endemic in many parts of the world but is not recognized as a zoonosis. The World Organization for Animal Health (OIE) periodically publishes disease distribution and outbreak maps. The sanitary status granted by the OIE has a profound economic impact in countries with meat trade-dependent economies because of the market restrictions that OIE imposes, especially on countries affected by FMD.

The FMD virus (FMDV) is a non-lipid-enveloped single strand RNA virus featuring an icosahedral symmetry and a described size (diameter) ranging from 28 to 40 nm. The virus belongs to the *Aphtovirus* genus, within the Picomaviridae family. The whole virus particle is extremely labile in vitro, it dissociates into monomers at temperatures above 56° C. and pH below 6. Seven FMDV serotypes have been reported, designated as O, A, C, SAT1, SAT2, SAT3 and Asia1.

Effective vaccines and stringent control programs have eradicated FMD in most developed countries but, regardless of strict international trade policies, major outbreaks have occurred relatively recently in Europe (2000, 2001) and in Japan (2000, 2010). FMD vaccines are manufactured in plants with NBS biological safety level 4 (OIE). It is estimated that between 2.5 and 3 billion doses are produced annually worldwide.

Rotaviruses are the most common cause of neonatal diarrhea in calves. Rotaviral diarrhea usually affects calves between four days to three weeks old. Calves are usually dull, and reluctant to drink. Over the course of the disease, which can last between 4 to 8 days, there is a significant risk of calf depression, dehydration and secondary infections. The calves will have a decreased appetite and may drool. The death rate can be as high as 50% without intervention.

The economic impact of calf diarrhea on the livestock industry is very substantial and far reaching: in addition to the costs associated with the additional labor, drug expenditures, and calf death, there is the potential economic impact associated with the poor long-term performance of affected calves. It has been found that 80% of calf morbidity from birth to day 21 is due to diarrhea.

Bovine rotavirus is a non-enveloped double-stranded RNA virus that belongs to the family Reoviridae. The virion has an icosahedral shape and features a triple protein capsid structures. The diameter of the virion has been described to be around 80 nanometers.

Vaccination of the dams against rotavirus represents an effective way to fight the disease and to prevent diarrhea in neo-natal calves. Calves should be fed colostrum from dams vaccinated against rotavirus infection 1-3 months before calving.

Infection of cattle by Bovine Herpesviruses can lead to severe diseases. Infectious Bovine Rhinotracheitis (IBR) is a highly contagious, infectious respiratory disease that is caused by Bovine Herpesvirus-1 (BHV-1 or BoHV-1). Bovine Herpesvirus 5 (BHV-5 or BoHV-5) differs from BoHV-1 in its tropism: BoHV-5 is the causative agent of meningoencephalitis in young cattle. BoHV-1 and BoHV-5 are enveloped double-stranded DNA viruses that belong to the *Varicellovirus* genus and to the Herpesviridae family. They have a spherical to pleomorphic shape and a described diameter of 150-200 nm. The internal protein capsid consists of 162 capsomers and is surrounded by an amorphous tegument.

IBR can affect young and older cattle. In addition to causing respiratory disease, this virus can cause conjunctivitis, abortions, encephalitis, and generalized systemic infections. IBR is characterized by the acute inflammation of the upper respiratory tract. After the first infection, the virus is never fully removed. It stays behind in nerve cells in the brain as a life-long latent (hidden) infection. However, at times of stress the virus can begin to multiply again and may be re-excreted, generally from the nose and the eyes. Therefore an animal which has been infected can never be considered safe. Purchase of infected animals is the main source of new infections. Diseases caused by the virus can be serious; therefore it is a barrier to international trade.

Since BHV-1 is a ubiquitous, highly contagious virus, vaccination is recommended as soon as passive immunity in calves has disappeared, usually around four to six months of age. Currently available vaccines for IBR include modified-live-virus (MLV) vaccines and inactivated or killed-virus (KV) vaccines.

Bovine Parainfluenza-3 (PI3) is a highly contagious respiratory disease prevalent in the cattle population. The disease is associated with the bovine respiratory disease complex (BRD).

Infection by PI3 virus (PIV-3) alone causes only mild diseases. The clinical signs include fever, cough, watery nasal and lacrimal discharge as well as increased rate of respiration and an increase breathing sounds. Infection can increase morbidity of other viral diseases such as bovine viral diarrhea and infectious bovine rhinotracheitis. The impact of PI3 infection is more significant when coupled with secondary bacterial pneumonia.

Parainfluenza-3 virus (PIV-3) is a negative-stranded RNA enveloped virus belonging to the *Respirovirus* genus within the Paramyxoviridae family. The virus has a spherical shape and a described diameter of about 150 nm.

Prevention through vaccination is the best way to prevent any large impact of Parainfluenza-3. Most PI3 vaccines are combined with other respiratory viruses like for example bovine herpesvirus-1 (BHV-1). The vaccine is available in modified live or inactivated form.

Rabies is a zoonotic disease transmitted from animals to humans, and caused by the rabies virus, of the *Lyssavirus* genus within the family Rhabdoviridae. The rabies virus is a negative-stranded RNA enveloped virus with a bullet like shape of about 180 nm in length and a cross-sectional diameter of about 75 nm.

All mammals are thought to be susceptible to the rabies virus. Domestic dogs are the most common reservoir of the virus, with more than 95% of human deaths caused by dog-mediated rabies.

The paralytic clinical manifestation of rabies is the most common form in cattle, pigs and horses. A bite from an infected wild animal, such as a fox or raccoon, is a common method of infection in cattle although the disease is also transmitted by hematophagous bats, a.k.a. "vampire" bats in tropical and subtropical areas. It is a serious threat to animal production with several thousand head of cattle losses each year and a human health concern because of contact between humans and rabid cattle during normal rearing operations.

With the exception of Antarctica, rabies is endemic in all continents. Of the tens of thousands of deaths occurring annually due to rabies, 95% of cases are reported in Asia and Africa.

Rabies is a 100% vaccine-preventable disease: safe and effective inactivated virus vaccines are available for dogs, cattle and humans. Post-exposure prophylactic vaccinations are required for treating individuals who have had no previous immunization.

Over the last decades, human and veterinarian health industries have witnessed increasingly stringent government regulations related to Good Manufacturing Practice (GMP) for the production of pharmaceutical and biopharmaceuticals products. New quality concepts have arisen, like Process Analytical Technology (PAT), which Food and Drug Administration (FDA) defines as a mechanism to design, analyze, and control pharmaceutical manufacturing processes through the measurement of Critical Process Parameters (CPP) that affect Critical Quality Attributes (CQA). PAT emphasizes the importance of controlling the production process as a means to achieve the highest quality standard for the final product. PAT represents an especially useful tool for the quality control of intermediate and final products in the vaccine industry. Indeed, the efficacy of inactivated virus vaccines, which are routinely used as part of eradication programs and in emergency contexts, is highly dependent on the antigenic payload formulated in each dose and on virus integrity.

As of today, the in-process quality controls of whole virus antigens in intermediate process streams relies mainly on the performance of titration assays when the virus is still alive (before the inactivation step) or on immunochemical methods like ELISA (Enzyme-Linked ImmunoSorbent Assay) or single radial immunodiffusion (SRID) tests and in some cases real-time quantitative PCR when the virus has already been inactivated.

ELISA detection kits are commonly used for the detection of disease-causative agents in body fluids, both for humans and animals. ELISA kits are generally designed to detect the antibody response to the infectious agents but not the infectious agents themselves. Although ELISA detection assays are used in some cases for the monitoring and quality control of viral antigens during manufacturing process, these assays have to be developed on a case by case basis and cannot be standardized to different kind of viruses as the conditions of the assay heavily relies on the detection reagents used in the kits, like monoclonal or polyclonal antibodies. The same is true for SRID assays.

Moreover, ELISA methods can yield only a rough quantification of virus particles based on the colorimetric titration of an antibody-antigen reaction. The results are greatly influenced by the dilution factor of the sample and the sample matrix. Consequently, the ELISA assay has to be adapted to the different kind of samples of the different manufacturing steps and cannot be considered as a useful tool for Process Analytical Technology (PAT).

In addition, ELISA assays or quantitative PCR methods do not yield any information on the size nor structural integrity of the virus particles, as both methods cannot discriminate between whole or ruptured viral antigens. Knowing the size and structural integrity of the virus particles are important to ensure the immunizing efficacy of vaccines.

For the FMD virus, the 140S (146S) quantitative sucrose density gradient analysis, as developed by Barteling and Meloen (Barteling S J, Meloen R H. *A simple method for the quantification of* 140*S particles of foot-and-mouth disease virus (FMDV)*. Arch Gesamte Virusforsch, 1974; 45(4):362-4), is the recommended method to quantify virus antigen and, on that basis, formulate vaccines. The principle of the 146S method is to separate the FMD viral particles based on their sedimentation coefficient in the sucrose gradient. Therefore, the technique provides only an indirect measurement of the integrity of the viral particles.

A number of international efforts have been attempted in order to standardize the method but there is as yet neither a harmonized protocol nor an international FMDV standard. The technical complexities of the method and the requirement of specialized items of equipment have probably contributed to this situation (Barteling S J. *Need for further standardization of the 146—S test as the basis for final—Foot-and-Mouth Disease (FMD) Vaccine formulation.* EUFMD Research Group Meeting 1999—Appendix 17).

The lack of a standardized method to measure the active ingredient present in viral vaccines is an important factor to explain why expensive and cumbersome clinical trials, typically involving large animals (the target species) or laboratory animals are still required for registration of viral vaccines and batch release.

For example in the case of the Rabies vaccine, the NIH potency test has been used over several decades as the reference assay for potency testing of vaccine batches. This cruel and highly complicated in-vivo assay requires the use of 150 mice per batch and includes the intracranial challenge of the mice with a pathogenic rabies strain.

Current international efforts working on the harmonization of methods for potency controls of vaccine and biopharmaceuticals molecules are focusing on the 3R principle: Reduction of the number of animals used; Replacement of animals with alternative technique, and Refinement of the ways experiments are carried out to make sure animals suffer as little as possible.

For the vaccine industry and especially for vaccines based on full-size antigens (like inactivated viral vaccines or live attenuated viral vaccines), methods and equipment capable of reliably quantifying and determining the size of particles in the nanometer (nm) range would represent important tools for the implementation of in-process controls meant to ensure the quality of the viral antigens produced at every step of the process. Nevertheless, the analysis of complex process streams containing virus particles is a much more difficult task than the analysis of common recombinant proteins like monoclonal antibodies (mAbs). One challenge is that manufacturing practices for many current vaccines were developed decades ago, before the rise of serum-free media culture technology. The serum containing medium used in many manufacturing processes contains a very high content of proteins. Also, the yield of virus particles obtained from the infection of cell culture is generally in the order of milligram per liters, which is several orders of magnitude lower compared to the expression of recombinant proteins such as mAbs. Also of great importance is the fact that some viruses have lytic replication cycle that triggers the destruction of the cell. The release in the cell culture medium of all the materials contained in the cytoplasm and the nucleus of the cells, including all the genomic material and lipid residues from the cell membrane will make the analysis more difficult.

Since size exclusion chromatography separates different molecules based on their hydrodynamic volumes, molecules of different molecular weights but similar hydrodynamic volumes are prone to show very similar mobility behavior during chromatography runs. In the conditions of very complex process streams, size exclusion chromatography is usually unable to provide a resolution good enough in order to separate the peak of virus particles of interest from other process contaminants of similar hydrodynamic volume such as large molecules of DNA and large lipid residues.

Protein or viral-based vaccines are vaccine models usually employed for delivering antigens to a subject for immunization. It is extremely crucial that the antigen being delivered is of its correct or native conformation such that appropriate epitopes can be presented to induce specific and effective immune responses. Therefore, misfolded, degraded or aggregated antigen may have reduced efficacy in, or even not be capable of, triggering specific immune responses.

Dynamic Light Scattering (DLS) helps to assess the efficacy of protein or viral-based vaccines in terms of their integrity and stability. By analyzing the DLS profile, one would be able to check whether the antigens have been degraded or aggregated over time or upon storage in a particular buffer or temperature, and thereby assuring the efficacy of the vaccines.

Separation methodologies such as size-exclusion chromatography, when used alone, usually give rough estimates of particle size by close scrutiny of mobility behavior but these assessments are not sensitive enough to detect subtle modifications of antigen dimension. In contrast, DLS sensitively and accurately detects and estimates size of particles, and hence allows monitoring subtle differences of the particles' size. However, DLS can only analyze the integrity and estimate the size of particles with high purity.

Due to the economic relevance of these livestock diseases worldwide, there is a continuous need of improvements in the prevention tools, particularly regarding improved vaccines and/or methods of preparation thereof. The present invention provides methods for the quantification and characterization of viruses, including the enveloped and non-enveloped viruses, and the RNA and DNA-based viruses, and related products in a high-throughput and accurate manner. With the growing demand for both quantity and quality of veterinary vaccines, the present invention is a very useful and cost-effective tool for the quality control of the viral vaccines.

As an example and in the case of Foot-and-Mouth Disease, the world biggest vaccine market, the Chinese market, requires 1.7 billion doses (of 2 milliliters each) per year. Considering that one average industrial batch of vaccine represents 5 million doses (i.e., a 10000 liters batch), this means that around 340 batches of FMD vaccines are produced each year in China by different manufacturers. As of today and because of this huge number of batches produced, the Chinese Veterinary Regulatory Authority has forfeited the responsibility of controlling the quality of the FMD vaccine batches and has to rely on the performance of quality control tests by each vaccine manufacturer. The quality control of FMD vaccines is usually monitored using in vivo potency testing which allows assessment of the quality of the vaccines in bulk quantity but requires complex and cumbersome procedures. Currently, there are no other in vitro techniques available that would enable the quality control of such a great quantity of batches of vaccine in a timely manner.

The present invention, for the first time, introduces an in vitro system that is capable of quantifying the antigen payload per dose and characterizing the size and the integrity of the viral antigen in each vaccine batch, in a high throughput manner, no matter if the antigen is a live-attenuated or inactivated virus. The present invention implements a much more simplified system than the in vivo potency testing system for the quality control of viral vaccines and thereby improves the quality of the products. It is estimated that the present invention can monitor the quality of 340 batches of vaccines in just a few days.

Thus, the present invention would eventually guarantee a better quality of the vaccines and confer a better protection against veterinary diseases to the animal and human population.

BRIEF SUMMARY OF THE INVENTION

In order to improve current methods and products for prevention of viral diseases (including but are not limited to foot-and-mouth disease, rotaviral diarrhea, infectious bovine rhinotracheitis, bovine herpetic encephalitis, bovine respiratory disease (BRD) complex and rabies), the present invention introduces a method for quantification and characterization of viruses by a combined use of a molecular exclusion chromatography and an in-line dynamic light scattering detection (DLS) for analysis of the chromatographic profile. The method described herein can quantify and characterize all viruses with high throughput and accuracy.

In one embodiment, the present invention provides a method to quantify and characterize the size and integrity of lipid enveloped and non-enveloped viruses. In another embodiment, the present invention provides a method to quantify and characterize the size and integrity of viruses having ribonucleic acids as the genetic materials (RNA viruses) or deoxyribonucleic acids as the genetic materials (DNA viruses).

In one embodiment, the present invention provides a method to quantify viral particles and to characterize their size and integrity in a complex process stream where some process contaminants cannot be separated from the viral particles by molecular exclusion chromatography only.

In one embodiment, the present method further comprises one or more sample preparation steps including a possible solvent extraction step using solvent such as chloroform, and an endonuclease digestion step using endonucleases such as Benzonase® or Turbo™ DNase before the molecular exclusion chromatography method and dynamic light scattering analysis.

In one embodiment, the present invention provides a method for isolating and purifying viral particles from products containing the particles.

In one embodiment, the present invention provides a method for designing and preparing formulation of products to prevent viral or veterinary diseases such as the foot-and-mouth disease, rotaviral diarrhea, infectious bovine rhinotracheitis, bovine herpetic encephalitis, bovine respiratory disease (BRD) complex and rabies.

In one embodiment, the present invention provides a method for evaluation of products containing viral particles, such as the quantity and stability of antigens. These products include but are not limited to antigen banks and vaccine containing those viruses.

In one embodiment, the present invention provides a method serving as an in-process quality control tool for determining the quantity and characterizing the integrity and size of viral antigens in intermediate products synthesized during the whole vaccine production process.

BRIEF DESCRIPTION OF THE DRAWINGS

FIG. 1A is the chromatographic profile tracked under 254 nm and FIG. 1B is the chromatographic profile tracked using Dynamic Light Scattering (DLS).

FIG. 2A is the chromatographic profile tracked under 254 nm and FIG. 2B is the chromatographic profile tracked using Dynamic Light Scattering (DLS).

FIG. 3A shows the chromatographic profile tracked under 254 nm of 2 samples: one sample treated with chloroform extraction and Benzonase® digestion and one sample without any treatment. FIG. 3B shows the chromatographic profile tracked under 254 nm of 2 samples both already treated with chloroform extraction: one sample further treated with Benzonase® digestion and the other sample without the Benzonase® digestion. FIG. 3C shows the chromatographic profile tracked under 254 nm of 2 samples both already treated with Benzonase® digestion: one sample further treated with chloroform extraction and the other sample without the chloroform extraction.

FIGS. 4A-4D show one embodiment of the quantification of a serial dilution of FMDV strain O1 Campos antigens which were prepared from an antigen concentrate obtained by an ultrafiltration concentration (UF). FIG. 4A shows the chromatographic profile tracked under 254 nm of an FMDV antigen O1 Campos concentrate obtained by ultrafiltration (UF). FIG. 4B shows the overlay of U.V. chromatographic profiles obtained from the five tested FMDV O1 Campos samples. FIG. 4C shows the overlay of the two chromatographic profiles of one FMDV O1 Campos sample: one profile tracked under U.V. 254 nm and the other profile using Dynamic Light Scattering (DLS). FIG. 4D shows the plots of FMDV O1 Campos viral concentration (µg/mL) and virus particle size (nm) versus the percent of dilution with regression line.

FIG. 5A shows the chromatographic profile tracked under 254 nm of a Bovine Rotavirus G6 antigen concentrate obtained by ultrafiltration (UF). FIG. 5B shows the overlay of U.V. chromatographic profiles obtained from the five tested Bovine Rotavirus G6 samples. FIG. 5C shows the overlay of the two chromatographic profiles of one Bovine Rotavirus G6 sample: one profile tracked under U.V. 254 nm and the other profile using Dynamic Light Scattering (DLS). FIG. 5D shows the plots of Rotavirus G6 viral peak area (mAU·mL) and virus particle size (nm) versus the percent of dilution with regression line.

Figures 6C, 6D:
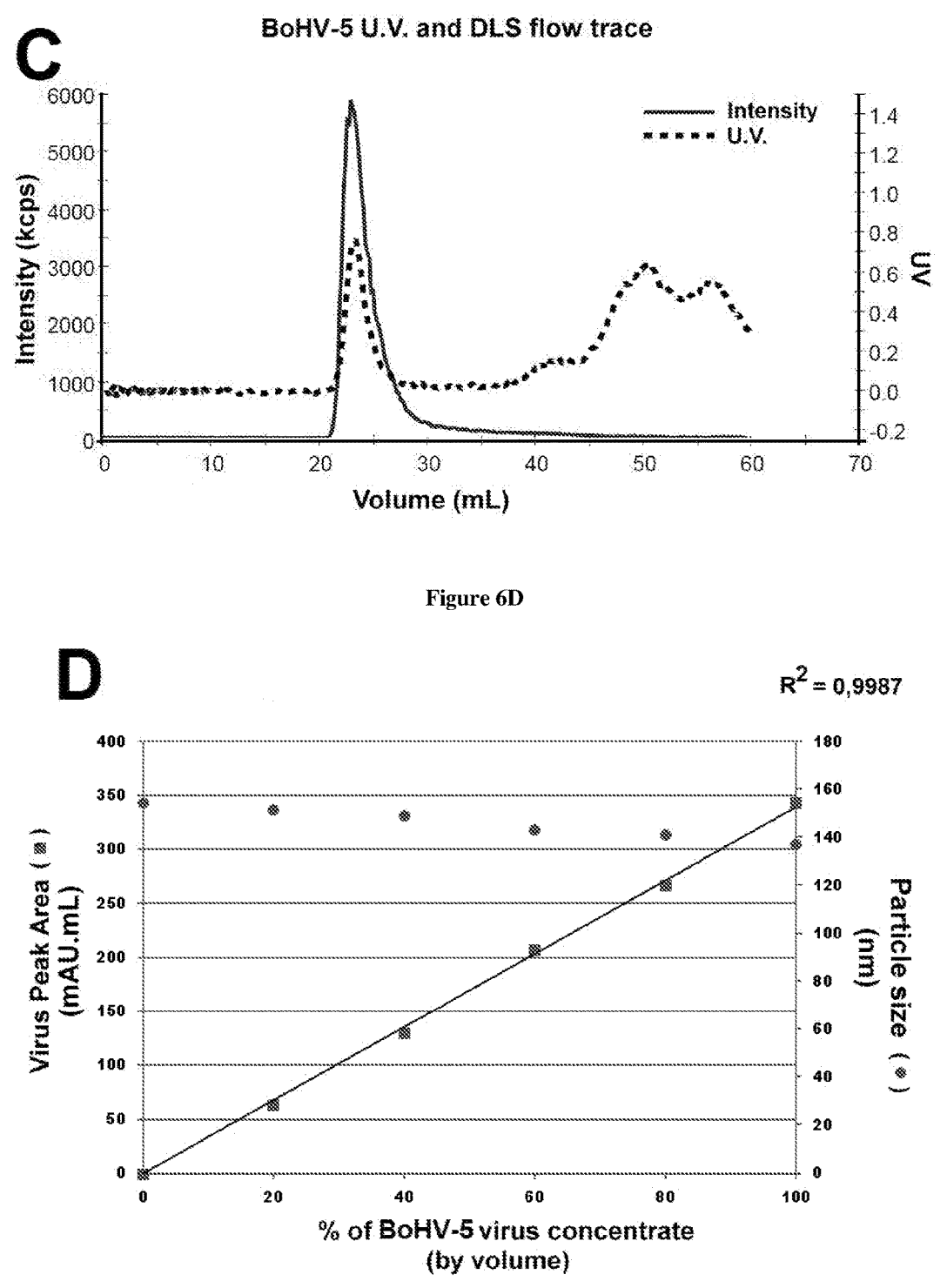

FIGS. 6A-6D show one embodiment of the quantification of a serial dilution of BoHV-5 antigens which were prepared from an antigen concentrate obtained by an ultrafiltration concentration (UF). FIG. 6A shows the chromatographic profile tracked under 254 nm of a BoHV-5 antigen concentrate obtained by ultrafiltration (UF). FIG. 6B shows the overlay of U.V. chromatographic profiles obtained from the five tested BoHV-5 samples. FIG. 6C shows the overlay of the two chromatographic profiles of one BoHV-5 sample: one profile tracked under U.V. 254 nm and the other profile using Dynamic Light Scattering (DLS). FIG. 6D shows the plots of BoHV-5 viral peak area (mAU·mL) and virus particle size (nm) versus the percent of dilution with regression line.

FIG. 7A shows the chromatographic profile tracked under 254 nm of a PIV-3 antigen concentrate obtained by ultrafiltration (UF). FIG. 7B shows the overlay of U.V. chromatographic profiles obtained from the five tested PIV-3 samples. FIG. 7C shows the overlay of the two chromatographic profiles of one PIV-3 sample: one profile tracked under U.V. 254 nm and the other profile using Dynamic Light Scattering (DLS). FIG. 7D shows the plots of PIV-3 viral peak area (mAU·mL) and virus particle size (nm) versus the percent of dilution with regression line.

FIG. 8A shows the chromatographic profile tracked under 254 nm of a Rabies virus antigen concentrate obtained by ultrafiltration (UF). FIG. 8B shows the overlay of U.V. chromatographic profiles obtained from the five tested Rabies virus samples. FIG. 8C shows the overlay of the two chromatographic profiles of one Rabies virus sample: one profile tracked under U.V. 254 nm and the other profile using Dynamic Light Scattering (DLS). FIG. 8D shows the plots of Rabies viral peak area (mAU·mL) and virus particle size (nm) versus the percent of dilution with regression line.

FIG. 9 shows a time course plot of a FMD O1 Campos virus infection in a 2000 liters cell culture bioreactor. It shows the changes in viral concentration (μg/mL), cell count ($10^6$ cell/mL) and the size of viral particles (nm) during the first eight hours after the infection.

FIG. 10 shows one embodiment of the schematics of a column-switching system which runs a Dynamic Light Scattering (DLS) detector and two size-exclusion chromatography (SEC) columns in parallel. The setups on the left and right panels can be switched back and forth.

DETAILED DESCRIPTION OF THE INVENTION

The present invention provides a method for quantification and characterization of viruses with high throughput and high accuracy.

In one embodiment, the present method is used to quantify and characterize the size and integrity of lipid enveloped and non-enveloped viruses. In another embodiment, the present method is used to quantify and characterize the size and integrity of viruses having ribonucleic acids as the genetic materials (RNA viruses) or deoxyribonucleic acids as the genetic materials (DNA viruses).

In one embodiment, the present method is used to quantify and characterize viruses including, but are not limited to, the Foot and Mouth Disease virus (FMDV) (all serotypes: O, A, C, SAT1, SAT2, SAT3 and Asia1), Bovine Herpesvirus 5 (BoHV-5), Bovine Herpesvirus 1 (BoHV-1), Parainfluenza 3 virus (PIV-3), Bovine Rotavirus such as serotypes G6 and G10, Rabies virus, Bovine Viral Diarrhea Virus 1 and 2 (BVDV-1 and BVDV-2), Bovine Respiratory Syncytial Virus (BRSV), Porcine Circovirus 2 (PCV-2). Porcine Reproductive and Respiratory Syndrome Virus (PRRSV), Porcine Parvovirus (PPV) and Bluetongue viruses (BTV).

In one embodiment, the present method is applicable to any virus listed in the literatures, public domain or websites, such as the report or "Virus Taxonomy" released by the International Committee on Taxonomy of Viruses (ICTV). The content of these publications are incorporated herein by reference.

With the combined use of two samples preparation steps of an optional solvent extraction and an endonuclease digestion with molecular exclusion chromatography, and a chromatographic profile analysis carried out by means of UV absorption at 250-280 nm and Dynamic Light Scattering (DLS) detectors, the method of the present invention provides an unexpectedly improved method for quantification and characterization of the integrity and size of viral particles for both enveloped and non-enveloped viruses, at every step of the manufacturing process of a vaccine.

The choice of the sample preparation steps depends on the type of viruses. In one embodiment as for non-enveloped viruses like FMDV and Bovine Rotavirus, the solvent extraction step is very useful to remove contaminating large lipid residues. In another embodiment as for lipid-enveloped viruses, like BoHV-5, PIV-3 and Rabies virus, the solvent extraction step cannot be performed as it will destroy the lipid envelop of these viruses and consequently destroy the viral particles.

The two sample preparation steps facilitate the separation of molecules and allow a high-throughput quantification and characterization of viral particles from all sources including the very complex process streams. Size exclusion chromatography (SEC) alone would not be able to separate the virus particles from contaminants such as large DNA molecules or large lipid residues that appear in these complex processes because these contaminants usually have hydrodynamic volumes similar to that of the virus particles. Also, the present method is advantageous over using size exclusion chromatography (SEC) alone for the characterization of the viral antigens since the latter can only provide an indirect and rough estimate of size based on elution volume from the chromatographic column.

The method of the present invention allows a rapid and accurate assessment of both the concentration and the quality of the viral antigens, wherein the quality is defined based on the structural integrity and size of the virus particles. With the precise and accurate measurement by Dynamic Light Scattering (DLS) the method described herein enables a more accurate estimation and a direct control of integrity and size of the viral antigens.

Calibrated SEC columns packed with chromatography media of a pore size that allows partial access of protein molecules, protein fragments and aggregates to the internal volume of the media can be used in order to assess polymerization and molecular fragmentation of highly purified proteins or peptides in biopharmaceutical preparations and products. However. DLS can only be used to analyze the integrity and size of particles with high purity. These techniques are not readily applicable in a high throughput format to more complex proteins solutions or in crude process intermediates that contain other kinds of contaminants like DNA or lipid molecules. It is because the limited resolution of the SEC in a short chromatographic run would not allow a sufficient separation of peaks of different species in the solution and therefore would not allow a good characterization of the sizes of different molecules. The present invention can be applied successfully to all kind of samples during the whole manufacturing process of virus particles or vaccine, and samples from other sources or processes. Examples include but are not limited to: a) during the infection of the cells cultured in a bioreactor (see Example 7) where the virus concentration is very low and the level of process contaminants is very high (e.g. proteins from bovine serum, proteins from lysed cells, cellular DNA and lipid residues released due to cellular membrane destruction); b) after the concentration of antigens in which the concentration factor can be as high as 150× or higher (see Examples 5-6); c) before formulation of the final vaccine in order to determine the appropriate payload of each vaccine dose, and d) on the final formulated product even in the cases of vaccines formulated as a water-in-oil emulsion (W/O) or water-in-oil-in-water double emulsion (W/O/W). The quantification and characterization technique described in the present invention can be applied to intermediate samples taken from very complex and crude processes as well as to highly purified virus reference standard with the same efficacy, accuracy and high throughput.

Figure 1A:
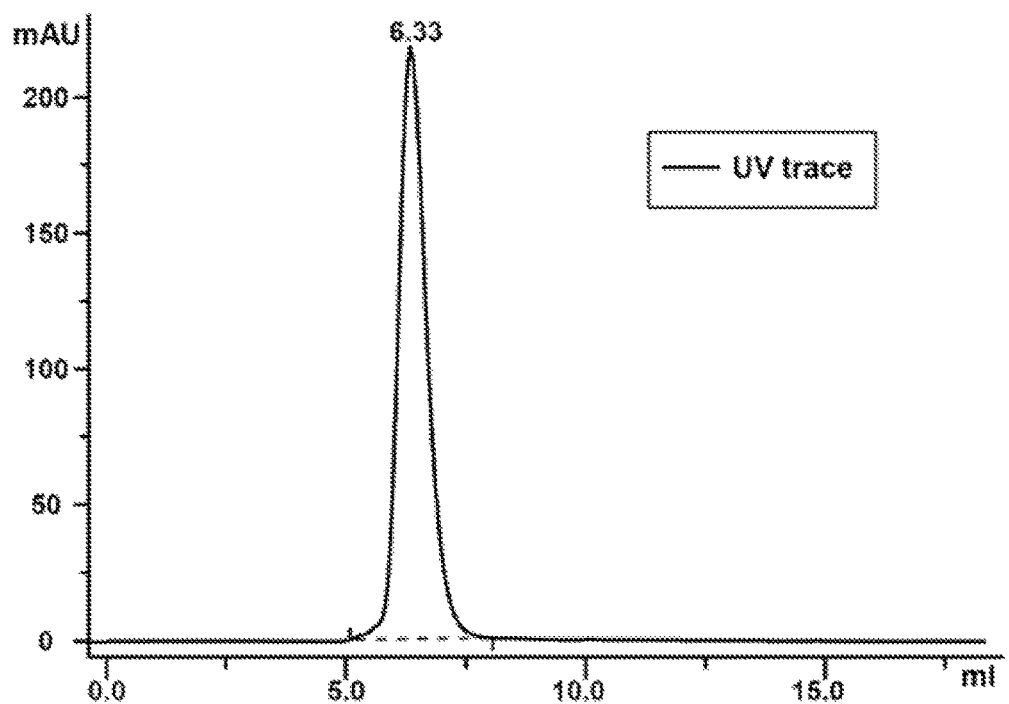
FIGS. 1A-1B show one embodiment of the chromatographic profiles of purified O1 Campos FMDV.

In one embodiment, the method of the present invention enables the analysis of both the quantity and the quality (e.g. integrity and size) of about 60 to about 70 samples of viral particles per day, a significantly higher throughput that is impossible to obtain in the case of employing other technique like Fast Protein Liquid Chromatography (FPLC) because of time constraints due to the long duration of one sample run (e.g. 3 hours) on the FPLC equipment. Therefore, the use of FLPC equipment allows a processing of a maximum of 4 samples per working day. On the other hand, the traditional 146S technique for FMD virus for example only allows for the analysis of a maximum of 12 samples per working day.

The method of the present invention is very significantly different from the prior techniques, because it can be applied successfully to samples prepared from all kind of processes including crude intermediates and purified viral samples, because it includes an in-line DLS detector that provides a direct estimation of integrity and size of the virus particle in question and can be run in a high throughput format.

In one embodiment, the present invention provides a multi-column switching mechanism that can be used in combination with the present methods or other applicable methods to further achieve a high samples throughput (see Example 8). In one embodiment, the present invention provides a column-switching system which is capable of running multiple columns and DLS detectors at the same time for a high throughput analysis. On the contrary, it is not feasible to implement the same technique in the case of the FPLC because FPLC usually involves a long duration of run, e.g. 3 hours per run.

Any change in the 3-dimensional structure especially in relation to the important epitopes of the antigen may decrease the immunogenicity of the antigen. The method of the present invention also enables a characterization of the antigen with high sensitivity, since it allows detection of small changes in the diameter of the viral antigens particles being quantified, while those small changes would be totally impossible to be detected with other techniques such as ELISA or SRID, sucrose gradient 146S technique, quantitative PCR or chromatography alone. Therefore, the present invention is capable of detecting small alterations in the size of antigens and provides a huge improvement for the characterization of the quality of an antigen.

In one embodiment, the present invention provides a method for quantification and characterization of whole viruses including but are not limited to Foot and Mouth Disease virus (FMDV), Bovine Herpesvirus 5 (BoHV-5), Parainfluenza 3 virus (PIV-3), Bovine Rotavirus and Rabies virus by high-performance liquid chromatography (HPLC). In one embodiment, the method comprises injecting a sample containing a virus such as Foot and Mouth Disease virus (FMDV), Bovine Herpesvirus 5 (BoHV-5), Parainfluenza 3 virus (PIV-3), Bovine Rotavirus or Rabies virus into a chromatographic column, eluting the sample, analyzing the chromatographic profile at a predetermined elution time range and determining the quantity, integrity and size of the virus particles.

In one embodiment, the chromatographic column is a molecular exclusion chromatography column.

In one embodiment, the chromatographic column is designed to separate particles with sizes in the range of 10-200 nm or higher and molecular weights in the range of $10^5$-$10^9$ Dalton or higher.

In one embodiment, the predetermined elution time range for the target virus is resolved by the chromatographic run of reference or standard samples of purified virus particles.

In one embodiment, the method described herein can quantify viral antigens or particles in a concentration range that is much broader than that attained by the current technologies, i.e. 5 to 70 μg/mL or 3 to 300 μg/mL. In another embodiment, the present method can quantify viral antigens or particles within the concentration of 1.2 to 750 μg/mL. In another embodiment, the present method can quantify viral antigens or particles higher than 750 μg/mL.

In one embodiment, the method described herein can characterize with great accuracy the size and integrity of viral antigens or particles independently of the concentration of the virus particles. In one embodiment with an in-line DLS, the present method can accurately measure the size of FMDV samples having a concentration ranging from 1.2 to 750 μg/mL, and the measurement is independent of the concentration of the FMDV antigens (see Examples 5 and 7). These results represent the first report of an accurate size and integrity characterization of FMD virus by an in-line DLS over such a broad range of concentrations.

As illustrated in the Examples as follow, the present method was thoroughly validated for the non-enveloped virus FMD virus (see Examples 5 and 7) with regard to reproducibility, specificity, linearity, accuracy, precision, and robustness. It represents the first validated in vitro technique available for the quantification of viral particles that also characterizes in-line the integrity and the size of the particles quantified. Since virus has a large size as compared to most components in a purified or crudely purified sample, virus may be isolated from low molecular weight components in the sample using conventional SEC techniques and eluted in the exclusion volume (or the void volume) of the column or very close to it, depending on the type of size exclusion column used. However, some high molecular weight components like large DNA molecules or lipid residues cannot be separated by SEC alone as these molecules have very similar hydrodynamic volume compared to viral particles. In addition, SEC or similar technologies cannot differentiate viruses that are slightly different in sizes. It is because most viruses are nearly excluded from the pores of the SEC and straightly passes through the column. Elution volumes of viruses of different sizes can be very similar. Offline DLS is of limited value to ascertain viral particle size because its results are strongly influenced by polydispersity. The presence of bigger and smaller particles in the sample may greatly affect the results. On the other hand, the combined use of DLS and SEC-HPLC relies on the high purity of the chromatographic peak to produce a direct particle size measurement unencumbered by other sample components; such size measurement cannot be inferred from the chromatographic mobility.

In one embodiment, the chromatographic profile analysis is carried out by means of UV absorption at 250-280 nm and Dynamic Light Scattering (DLS) detectors. In another embodiment, the chromatographic profile analysis is carried out by means of in-line Dynamic Light Scattering (DLS) detectors. The present method features an in-line Dynamic Light Scattering detector that enables real-time analysis of the whole size exclusion chromatographic profiles and thereby allows a rapid and accurate assessment of both the concentration and the quality of the viral antigens.

In one embodiment, the chromatographic profile analysis of a viral sample is carried out by a comparison to a predetermined size distribution of integral viral particles. Reference or standard samples containing purified viruses are analyzed by chromatography and in-line DLS analysis, thereby resolving the sizes of each viral strain and generating predetermined size distribution of viral particles.

In one embodiment, the chromatographic profile analysis of a purified sample allows differentiation of whole integral viral particles from disintegrated viral fragments. For example in the case of FMDV, the present method allows differentiation of whole FMDV particles from the disintegrated fragments such as 12S particles or capsomers.

In another embodiment, the chromatographic profile analysis enables a detection of size deviation of viral particles such as a Foot and Mouth Disease virus (FMDV), Bovine Herpesvirus 5 (BoHV-5), Parainfluenza 3 virus (PIV-3), Bovine Rotavirus or Rabies virus in a sample as compared to the reference sample(s) of the same virus and strain.

In one embodiment, the chromatographic profile analysis enables quantification and characterization of size and integrity of viruses like Foot and Mouth Disease virus (FMDV), Bovine Herpesvirus 5 (BoHV-5), Parainfluenza 3 virus (PIV-3), Bovine Rotavirus and Rabies virus viral particles of up to 57 samples per working day. In one embodiment, the chromatographic profile analysis enables quantification and characterization of size and integrity of viruses like Foot and Mouth Disease virus (FMDV), Bovine Herpesvirus 5 (BoHV-5), Parainfluenza 3 virus (PIV-3), Bovine Rotavirus and Rabies viral particles of up to 72 samples per working day.

In one embodiment, the FMDV sample includes, but not limited to, a supernatant of an FMDV infected cell culture, an intermediate product from the vaccine manufacturing process, an antigen batch or bank, a vaccine, a monovalent vaccine batch or a multivalent vaccine batch.

In one embodiment, the Bovine Rotavirus sample includes, but not limited to, a supernatant of an Rotavirus infected cell culture, an intermediate product from the vaccine manufacturing process, an antigen batch or bank, a vaccine, a monovalent vaccine batch or a multivalent vaccine batch.

In one embodiment, the BoHV-5 sample includes, but not limited to, a supernatant of an BoHV-5 infected cell culture, an intermediate product from the vaccine manufacturing process, an antigen batch or bank, a vaccine, a monovalent vaccine batch or a multivalent vaccine batch.

In one embodiment, the PIV-3 sample includes, but not limited to, a supernatant of an PIV-3 infected cell culture, an intermediate product from the vaccine manufacturing process, an antigen batch or bank, a vaccine, a monovalent vaccine batch or a multivalent vaccine batch.

In one embodiment, the Rabies virus sample includes, but not limited to, a supernatant of an Rabies infected cell culture, an intermediate product from the vaccine manufacturing process, an antigen batch or bank, a vaccine, a monovalent vaccine batch or a multivalent vaccine batch.

In one embodiment, the non-enveloped virus samples, like FMDV or Bovine Rotavirus, are optionally pre-treated with a solvent prior to the injection into the chromatographic column. In one embodiment, solvent used herein is a non-polar or a lipid-soluble solvent including, but is not limited to, chloroform, benzene, toluene, hexane, pentane and octane. In one embodiment, solvent used here is a polar organic solvent including, but is not limited to, methanol, ethanol, isopropanol, dichloromethane, acetone and acetonitrile. In one embodiment, one or more types of solvent are used together for pre-treating the samples.

In one embodiment, the enveloped or non-enveloped virus sample is pre-treated with one or more enzymes prior to the injection into the chromatographic column. In one embodiment, the enzyme is a nuclease including but is not limited to a DNase, RNase, endonuclease, exonuclease and restriction endonuclease. In one embodiment, the enzyme is Benzonase®, TURBO™ DNase, T7 endonuclease, S1-nuclease, P1-nuclease, and Endonuclease I. The nuclease cuts the large DNA molecules into smaller DNA molecules which can be subsequently separated by the chromatographic column.

In another embodiment, the monovalent vaccine or multivalent vaccine is pre-treated in order to remove adjuvants prior to the optional treatment with a nuclease.

In one embodiment, the reference or standard sample(s) of purified virus for each type or strain are prepared by infecting a mammal cell culture with the virus, inactivating the produced virus with a chemical agent, and one or more of: ultracentrifugation on sucrose gradient, ultrafiltration, ion exchange chromatography or molecular exclusion chromatography.

In another embodiment, the reference or standard sample of purified virus is prepared by removing the adjuvant from a reference vaccine containing the same virus.

In one embodiment, the present invention provides a method for isolating and purifying viral particles from products containing the viral particles.

In another embodiment, the present invention provides a method of in-process quality control for determining the quantity and characterizing the integrity and size of viral antigens including, but are not limited to, the Foot and Mouth Disease virus (FMDV). Bovine Herpesvirus 5 (BoHV-5), Parainfluenza 3 virus (PIV-3). Bovine Rotavirus and Rabies virus antigens produced at every step of the manufacturing process of a viral vaccine. With a combined use of size exclusion chromatography and in-line DLS detection, the present invention also provides a tool for monitoring the kinetics of infection during the production process of the viral antigen (see Example 7). By checking both the quantity and the quality (e.g. integrity and size) of the live virus, the present invention enables a high-level of in-process control, in accordance with the international guidelines of Process Analytical Technologies (PAT) which is the highest quality standard in the production of veterinary vaccine.

In one embodiment, the present method is capable of detecting whether the specific viral products are contaminated by other viruses. Sometimes, cells used for the production of enveloped or non-enveloped virus may be contaminated by other different viruses or pathogens which can also propagate in the cell culture substrate. SEC alone may not be able to remove or even detect the contaminating viruses since most viruses are large in size, and therefore both the specific virus of interest and the contaminating viruses will be eluted at the exclusion volume of the column. In contrast, the present invention is capable of detecting the presence of contaminating viruses or other pathogens that have a different size than the specific desired virus by analyzing the DLS profile. For example, viruses that are larger than the specific virus of interest will lead to an increase in dispersed light intensity and/or Z-average in the peak. It is also possible to quickly assess the degree of contamination by comparing the DLS profiles of the contaminated and non-contaminated samples. As illustrated in FIGS. 4-8, the five viruses tested in the present application each has its own characteristics U.V. and DLS profiles, indicating that the present invention can sensitively differentiate different types of viruses or pathogens. Therefore, the present invention is capable of determining whether a sample has been contaminated by other molecules such as other viruses, pathogens or other contaminants that resulted in chromatographic profiles or readings deviated from the normal ones.

In one embodiment, the present method is used to assess if significant variations exist between various batches of viral vaccines or products by comparing their U.V. and DLS profiles. A constant set of U.V. and DLS profiles would indicate the process stream is normal and the quality of products is maintained. Any detectable differences in the U.V. or DLS profiles may indicate an error or a deviation from the normal process stream or a possible contamination. This would ultimately provide a better quality control to ensure the consistent quality and efficacy of the products.

In another embodiment, there is provided a method for evaluating viral antigen-containing products by determining the stability of the viral antigen. The evaluation method comprises quantification and characterization of the integrity and size of viral particles in a sample at two different time points by means of the method of the present invention and quantification of changes occurred in the sample and deviation in size and/or integrity of the viral particles during the two time points in order to measure the stability of the viral antigen. The present method can also be used to characterize viral particles stored at different temperatures or in different buffers or formulated with different adjuvants.

In another embodiment, the present invention provides a method to evaluate and prepare monovalent or multivalent vaccine against diseases such as the Foot and Mouth Disease caused by FMDV, neonatal calves diarrhea caused by Bovine Rotavirus G6 or G10, Infectious Bovine Rhinotracheitis caused by BoHV-1, Bovine Herpetic Encephalitis caused by BoHV-5, respiratory diseases caused by PIV-3 and Rabies caused by the Rabies virus. By using the method described herein, quantification of the antigenic payload per dose and characterization of the integrity and size of the antigens formulated in the vaccine can be performed.

It should be noted that all of the methods and systems described herein can be applied to all types, subtypes or strains of viruses, no matter the viruses are known or unknown, or the viruses are purified or contaminated with other molecules. The description and examples on the five viruses provided herein are for illustrative purpose to show the technical effects and advantages of the present invention, and do not be meant to limit the invention as claimed. One of ordinary skill in the art can adjust the present methods and systems according to the present disclosure to suit specific need of quantification and characterization.

In one embodiment, the present invention provides a method for quantification and characterization of one or more types of viruses or viral particles, comprising the steps of (a) treating specimens comprising said viruses or viral particles with one or more enzymes to obtain a plurality of viral samples; (b) applying a first viral sample to a chromatographic system comprising a plurality of pumps and a plurality of chromatographic columns, wherein (i) a first pump is connected to a first chromatographic column via a first valve, said first column is further connected via a second valve to a detection system comprising a Dynamic Light Scattering (DLS) detector and an UV detector; and (ii) a second pump is connected to a second chromatographic column via said first valve, said second column is further connected via said second valve to a waste collector, wherein the first viral sample is run through the first column while a washing buffer is run through the second column; (c) eluting the first viral sample from the first column and obtaining chromatographic profile for quantification and characterization of the first viral sample by said detection system; (d) switching connections for said first and second pumps so that (i) said first pump is now connected to said second column via said first valve, said second column is further connected via said second valve to said detection system; and (ii) said second pump is now connected to said first column via said first valve, said first column is further connected via said second valve to a waste collector; (e) applying a second viral sample to the second column while applying a washing buffer to the first column; (f) eluting said second viral sample from said second column and obtaining chromatographic profile for quantification and characterization of said second viral sample by said detection system; and (g) repeating the steps of (b) to (f), thereby obtaining quantification and characterization of said plurality of viral samples.

In one embodiment, said viruses or viral particles are enveloped viruses, non-enveloped viruses, DNA viruses, RNA viruses, live viruses, live-attenuated viruses, inactivated viruses, recombinant viruses, viral vectors, or virus-like particles. In one embodiment, the viruses are Foot and Mouth Disease viruses (FMDV), Bovine Herpesviruses 5 (BoHV-5), Bovine Herpesviruses 1 (BoHV-1), Parainfluenza 3 viruses (PIV-3). Bovine Rotaviruses, Rabies viruses, Bovine Viral Diarrhea Virus, Bovine Respiratory Syncytial Virus (BRSV), Porcine Circovirus 2 (PCV-2), Porcine Reproductive and Respiratory Syndrome Virus (PRRSV), Porcine Parvovirus (PPV) or Bluetongue virus (BTV).

In one embodiment, the first and second viral samples comprise the same type of viruses or viral particles. In another embodiment, the first viral sample comprises viruses or viral particles different from those of the second viral sample.

In one embodiment, the above specimens are supernatant of virus-infected cell cultures, an intermediate product from a vaccine manufacturing process, an antigen batch or bank, a vaccine, a monovalent vaccine batch, or a multivalent vaccine batch.

In one embodiment, the enzymes used in the above method are endonucleases, exonucleases, restriction enzymes, DNases or RNases.

In one embodiment, the treatment with one or more enzymes in step (a) removes molecules interfering the quantification and characterization of said viruses. In another embodiment, the above specimens are treated in a solvent before or after treating with said one or more enzymes in step (a). For example, the solvent is a non-polar solvent such as chloroform, benzene, toluene, hexane, pentane, or octane.

In one embodiment, the above chromatographic system comprises two chromatographic columns. In another embodiment, the chromatographic system comprises three chromatographic columns.

In one embodiment, the chromatographic system further comprises an autosampler to inject said viral samples to the chromatographic columns. In another embodiment, the chromatographic system further comprises one or more systems to integrate and control the functioning of the plurality of components of the chromatographic system.

In one embodiment, the above quantification and characterization of viruses comprise determining the size and integrity of said viruses or viral particles. In one embodiment, the chromatographic profile is compared to a chromatographic profile derived from a reference sample of purified viruses, or compared to a chromatographic profile derived from whole integral viral particles to allow differentiation of whole integral viral particles from disintegrated viral fragments.

In one embodiment, the above chromatographic columns are designed to separate particles with sizes in the range of 10-200 nm and molecular weights in the range of $10^5$-$10^9$ Dalton.

In one embodiment, the above method is capable of analyzing the chromatographic profiles of up to about 60-70 samples per day.

In one embodiment, the above method separates large DNA molecules, lipid molecules and viral particles having similar elution volumes as eluted from the chromatographic column. In one embodiment, the quantification of viruses is independent of the concentration of the viruses in said viral samples.

In one embodiment, the concentration of FMDV particles present in the sample is from about 1.2 to about 750 µg/mL.

The present invention also provides a system for high-throughput quantification and characterization of samples containing virus particles, comprising an autosampler for sample injection; two or more chromatographic columns for separating the viral particles, wherein the two or more chromatographic columns are of the same type or of different types; two or more pumps for driving the two or more chromatographic columns; at least one ultraviolet detector for producing a chromatographic profile of the eluted viral particles and determining the quantity of said eluted viral particles; at least one Dynamic Light Scattering (DLS) detector for determining the size and integrity of the eluted viral particles; a waste collector for collecting liquids eluted from the chromatographic columns; and a multiple-valve array comprising two or more valves to connect the plurality of components of the system.

In one embodiment, the above system analyzes the chromatographic profiles of viral particles including the enveloped and non-enveloped viral particles, eluted sequentially from each of the two or more chromatographic columns, thereby determining the quantity, size and integrity of the viral particles in a high-throughput and real-time manner. In another embodiment, the system further comprises one or more control systems for integrating and controlling the functioning of the plurality of components of the system.

The invention will be better understood by reference to the Experimental Details which follow, but those skilled in the art will readily appreciate that the specific experiments detailed are only illustrative, and are not meant to limit the invention as described herein, which is defined by the claims which follow thereafter.

Throughout this application, various references or publications are cited. Disclosures of these references or publications in their entireties are hereby incorporated by reference into this application in order to more fully describe the state of the art to which this invention pertains. It is to be noted that the transitional term "comprising", which is synonymous with "including", "containing" or "characterized by", is inclusive or open-ended and does not exclude additional, un-recited elements or method steps.

Example 1

Preparation of Reference Samples of FMDV

This example illustrates the procedure for preparing reference samples of FMDV for generating predetermined volume (or time) of elution and predetermined size distribution of FMDV particles.

Solutions Used:
Dialysis Membranes Conditioning Buffer:
Volume: 1 L
Composition: 10 mM $NaHCO_3$; 1 mM EDTA.
Dialysis Buffer:
Volume: 5 L
Composition: 100 mM NaCl; 50 mM Tris Base; pH=8
Tris Buffer:
Volume: 5 L
Composition: 200 mM NaCl; 20 mM Tris Base; pH=8
Viral Suspension:
Volume: 200 mL
Composition: FMDV strain O1 Campos
Procedures:
Step 1: Dialysis.
This step was performed to reduce the ionic strength of the suspension of the virus to allow subsequent enzymatic digestion, without increasing the volume of the sample.
1. Boiled the dialysis bags in the dialysis membranes conditioning buffer for at least 30 minutes in a glass beaker. Rinsed 5 times with water and stored at 4° C. until use.
2. Closed the lower end of the dialysis bags and fill in samples.
3. Dialyzed the viral suspension samples four times against 800 mL of the dialysis buffer at 4° C. for 2 hours each time.
4. Dialyzed the viral suspension samples against 1800 mL of the dialysis buffer 4° C. for overnight.
Step 2: Enzymatic Digestion.
This step was performed to remove nuclease-sensitive impurities from the samples.
1. Enzyme Preparation: at the time of use, diluted 25 µL Benzonase® (250 U/µL) in 10 mL of dialysis buffer preheated to 37° C. Final concentration of the enzyme dilution: 25 L×250 U/µL=6250 U/10 mL=625 U/mL of Benzonase®.
2. Digestion: Fractionated the dialyzed viral suspension into centrifuge tubes of 50 mL, at 24 mL per tube. Added to each tube 1 mL of the enzyme dilution. Sealed the tubes and placed the tubes horizontally in an orbital platform shaker preheated at 37° C.
3. Stirred the samples sufficiently for 2 hours for a good agitation of the suspension, but avoid foaming.
Step 3: Desalting by Gel Permeation Chromatography
This step was performed to exchange buffer of the reference samples and eliminate low molecular weight components from the reference samples.
1. Equilibrated Sephacryl S-300 media with two washes of 500 mL of Tris buffer and re-suspend the media in a final volume of 230 mL. The total volume of packed resin was 150 mL and the total volume of the preparative column was 250 mL.
2. Packed the preparative column chromatography with equilibrated Sephacryl S-300 resin:
   a. Poured 230 mL of the suspension into the column.
   b. Allowed the resin to decant by gravity overnight.
   c. Placed the metallic mesh disc on the gel.
   d. Added 25 mL of Tris-Salts buffer on the metal mesh.
   e. Connected the reservoir with Tris buffer.
   f. Passed 200 mL of the buffer to the reservoir.
   g. Disconnected the reservoir from the Tris buffer.
   h. Opened the drip of the column until the buffer just reached the level of the mesh and then closed the drip.
Desalting/Elimination of Low Molecular Weight Components:
   a. Loaded 43 mL of sample onto the gel.
   b. Opened drip and allowed the sample to enter the gel.

c. Loaded column with 60 mL of Tris buffer. Opened drip and collected the eluate containing the virus. Stored the eluate at 4° C.
d. Equilibrated the column with 300 mL of Tris buffer.
e. Repeated above until you finished passing all the samples. If the final sample volume to be loaded in the column is less than 43 mL, make up the sample volume to 43 mL with Tris buffer before loading it to the column.
f. Prepared a pool of collected eluates.
g. Performed a final column wash with 300 mL of Tris buffer. Unpacked the column and washed the resin two times with 500 mL of 20% ethanol each time.

Step 4: Evaluation of Reference Samples

Eluates obtained from step 3 were subject to sucrose gradient centrifugation, UV spectrophotometric titration and size exclusion chromatography to evaluate whether a purified sample of FMDV particles has been prepared.

Example 2

Quantification and Characterization of FMDV Particles

This example illustrates one embodiment of the present invention for quantifying and characterizing the integrity and size of FMDV particles in intermediate process samples, independently of their purity, and in the finished product, the FMD vaccine, using Dynamic Light Scattering (DLS). In one embodiment, the U.V. trace is used to determine the peak area for calculating the viral concentration, whereas the DLS is used to characterize the size and integrity of viral particles.

Equipment and Operating Conditions:
  Infinity Agilent 1260 chromatograph equipped with pump, online degasser, autosampler, sample cooling module, column thermostat, UV detector of variable wavelength and PC Edition OpenlabCDS Chemstation software.
  Chromatography column: TOSOH Bioscience TSKgel G4000PWXL (7.8 mm ID×30.0 cm L) or equivalent optionally equipped with guard column TSKgel PWXL Guardcol (6.0 mm ID×4.0 cm L) or equivalent and cartridge Phenomenex SecurityGuard GFC AJO-4489-4000.
  Eppendorf Thermomixer Interchangeable block for 24×1.5 mL block.
  GPC1 mobile phase (30 mM Tris, 400 mM NaCl. pH=8).
  Benzonase®, Sigma E1014—25KU—≥250 units/µL, ≥90% (SDS-PAGE).
  Benzonase® dilution buffer (50 mM Tris, 20 mM NaCl, 2 mM $MgCl_2$).
  Working dilution of Benzonase® (1.25 U/µL).
  Dilution Buffer 30 mM Tris, pH=8.
  Malvern Zetasizer Nano S Dynamic Light Scattering (DLS) ZEN1600 analyzer with Zetasizer v. 7.02 software.
  Flow-mode operation kit with flow cell Hellma Analytics 176.751-QS ZEN0116.

Analysis Procedure:
a) Pre-Treatment of Samples
  i. Chloroform Extraction
  (1) Supernatants of Cell Culture Infections, Aqueous Phase Before Formulation of the Emulsion and Ultrafiltration Concentrates.
  5 mL of sample were fractionated into 15 mL centrifuge tubes and 5 mL of chloroform were added. Samples and chloroform were vigorously shaken for 2 minutes and then centrifuged at 4500 RPM for 15 minutes at 4° C. Aqueous upper layer was transferred to a fresh 15 mL tube. Chloroform extraction was repeated for a second time and upper layer recovered again into yet another fresh tube. For ultrafiltration virus concentrates a further dilution was performed adding 1 mL of a Tris 30 mM, pH=8 solution to 2 mL of chloroform extracted sample in order to reduce the sample ionic strength before enzymatic digestion.
  (2) Viral Concentrates Prepared by PEG Precipitation.
  10 mL of viral concentrate was sampled under constant vigorous magnetic stirring to keep precipitate from settling. The sample was transferred to a 250 mL beaker and diluted to a final volume of 100 mL with 30 mM Tris, 100 mM NaCl. pH=8 and magnetically stirred overnight at 4° C. 5 mL of the diluted concentrate was submitted to the chloroform extraction as described in the previous paragraph.
  (3) Water-in-Oil Emulsion FMD Vaccine.
  20 mL of commercial oil-based vaccine were fractionated in a 50 mL centrifuge tube. 20 mL of chloroform were added to the tube; it was shaken vigorously for 5 minutes and then centrifuged at 4500 RPM for 15 minutes at 4° C. The aqueous phase was separated and transferred to another 50 mL tube. A second portion of 20 mL of chloroform was added to the tube, shaken vigorously for 5 minutes and centrifuged at 4500 RPM for 15 minutes at 4° C. The aqueous phase was separated and transferred to another 50 mL tube. This recovered aqueous phase is the sample to be analyzed for water-in-oil emulsion FMD vaccine.
  ii. Enzymatic Digestion
  The recovered samples can be used directly or subject to pretreatment as described in the previous section, when appropriate. 1 mL of the sample obtained in the recovery procedure (i) was transferred to a 1.5 mL Eppendorf tube. 20 µL of working dilution of Benzonase® (1.25 U/µL) i.e. 25 U of Benzonase® were added to the tube, and it was shaken at 37° C. at 1400 RPM (high speed) in Eppendorf Thermomixer for 60 minutes. The sample tube was removed from the Thermomixer and centrifuged at 16000 g at 4° C. for 10 minutes. The supernatant was harvested from the tube, taking care of not disturbing the pellet, and loaded into a HPLC vial which was finally capped. Reference or calibration sample(s) prepared as described above was used directly or pre-treated in the same manner as the tested samples before performing chromatographic analysis. The temperature regulated, microprocessor-controlled, high-speed orbital mixer for microcentrifuge tubes from Eppendorf allows performing enzymatic digestion for up to 24 digestions simultaneously with the reduced sample volume requirements of HPLC.

b) Chromatographic Analysis
  The sequence of samples to be injected was scheduled with the appropriate method for each sample type. The chromatographic elution line was connected: samples were run through the chromatography column, the U.V. detector and then the Hellma flow cell in the ZEN1600 DLS analyzer. Appropriate playlist was set in the Zetasizer software of the DLS analyzer. The peak of virus with a retention time of approximately 15 to 16 minutes (or corresponding volume of elution) was integrated (the exact time depends on the chromatographic elution conditions used). Concentration of FMDV in the control samples was determined according to the following equation:

$$\text{FMDV } [\mu g/mL] = (\text{Area} \times 10 \times 1.02)/(F_t \times 72 \times b \times \text{Vol}_{inj})$$

Where:

Area: is the area under the curve. It may have units of mAU*s, mAU*min or mAU*mL 10: is a unit conversion factor.

1.02: is a dilution correction factor for Benzonase solution addition, if applicable.

72: is the published mass absorptivity coefficient $_{254}E^{1\%}$ of FMDV.

$F_t$: is the flow-time factor, equal to 120 for Area in mAU*s, 2 for Area in mAU*min and 1 for Area in mAU*mL for a 0.5 mL/min chromatographic flow.

b: is the optical path length of the U.V. flow cell in cm.

$Vol_{inj}$: is the injected volume in mL.

For the ultrafiltration virus concentrates the result was multiplied by a factor of 1.5 to take into account the 2/3 dilution required before enzymatic digestion.

The plot Flow Trace vs. Volume/Time plot was generated in the DLS Zetasizer software. The FMDV peak signal was identified by its elution time/volume and the Z-average diameter (d·nm) of the peak was recorded.

The validity of the whole analysis procedure was confirmed by the following parameters: a) the slope of the calibration curve, obtained with the control samples, was 86.4 (mAU*s)/(mg/mL)+/−8.64; b) the absolute value of the x-intercept was less than 10% of the average concentrations of the control samples and c) the FMDV peak Z-average diameter is between 28 and 40 nm.

In one embodiment, the present method is validated based on parameters such as selectivity, peak purity, accuracy, linearity of response, repeatability, intermediate precision and limits of detection and quantification determined from FMDV reference or standard samples of the same viral strain. In one embodiment, two reference or standard samples each representing a high or a low quantity of FMDV are included in every test for validation purposes. In one embodiment, one or more virus-free negative controls such as a mammalian cell sample which has been lysed by freeze/thaw cycles and pre-treated similarly as the FMDV samples were included in the test to validate the result.

Once the test was confirmed valid, the value of the tested samples was determined by direct calculation or by extrapolation of the area value obtained in the calibration curve established with the control samples.

In one embodiment, the length of column used in the present invention is 30 cm. In general, a shorter column provides a shorter run but a lower resolution especially for particles with similar hydrodynamic volumes. One of ordinary skill in the art can adjust the length of column according to type of samples of interest.

In one embodiment, a TOSOH Bioscience TSKgel G4000PWXL size-exclusion column is used to sufficiently isolate the FMDV particles from the contaminants in a short chromatographic run. Depending on the nature of the samples, resins of other pore sizes or in other forms or materials can be used to prepare the present size-exclusion column. However, it should be noted that, the pore size of resin does not only affect the resolution of the separation but also affect the total run time. For example, it would take a longer time to elute the FMDV if the pore size is big enough for the virus to enter, and therefore lengthen the whole separation process.

Interpretation of Results

Analysis of Purified O1 Campos FMD Virus Reference Sample and Evidence of its Disintegration after Heat Treatment This example shows direct evidence on how the method of the present invention enables quantification and the characterization of the integrity and size of FMD virus particles.

This example shows as well how the method of the present invention could detect fragments (12S or capsomers) of the disintegrated particles after the heat treatment and nuclease (Benzonase®) digestion of the purified O1 Campos FMDV reference sample.

FIG. 1A shows the chromatographic profiles at U.V. 254 nm of purified O1 Campos FMDV. The chromatographic profile shows a single peak with an elution volume of 6.33 mL. Calculation of the virus concentration based on the area under the curve yielded a concentration of 421.7 µg/mL, using the formula: FMDV [µg/mL]=(Area[mAU*mL]×10)/(1×72×0.5 [cm]×0.1 [mL]). Table 1 lists the parameters output from the UV chromatographic analysis of the elution peak.

TABLE 1

Chromatographic parameters of purified O1 Campos FMDV

| Peak | Elution Volume (ml) | Area (mAU * ml) | Height (mAU) |
|---|---|---|---|
| 1 | 6.33 | 147.1057 | 217.037 |

Figure 1B:
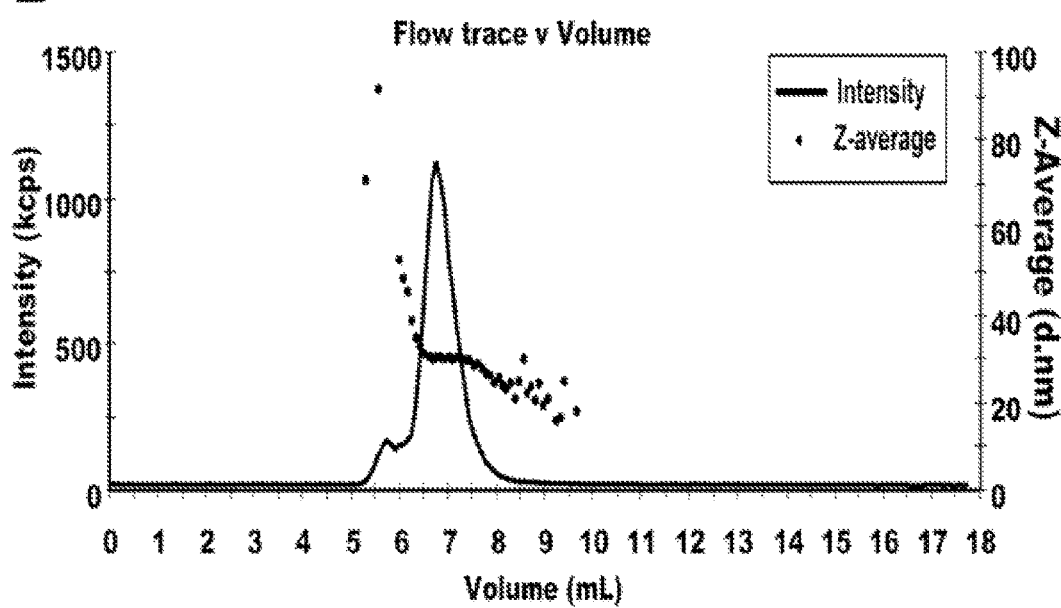

The light scattering intensity trace, as presented in FIG. 1B (solid line), recorded in the DLS detector also shows a single peak with a slight skew to the left in the same volume range. Z-average trace (dots) indicates that this peak is produced by particles with an average diameter of 29.28 nm. This measurement is consistent with the known diameter of FMDV viral particle size. Table 2 lists the parameters output from the DLS analysis of the elution peak.

TABLE 2

DLS analysis of purified O1 Campos FMDV

| Peak | Start volume (mL) | End volume (mL) | Size (d · nm) | % Int. | DLS SD (d · nm) | Estimated MW (kDa) |
|---|---|---|---|---|---|---|
| 1 | 6.56 | 7.3 | 29.28 | 100.0 | 2.271 | 1800 |

Figure 2A:
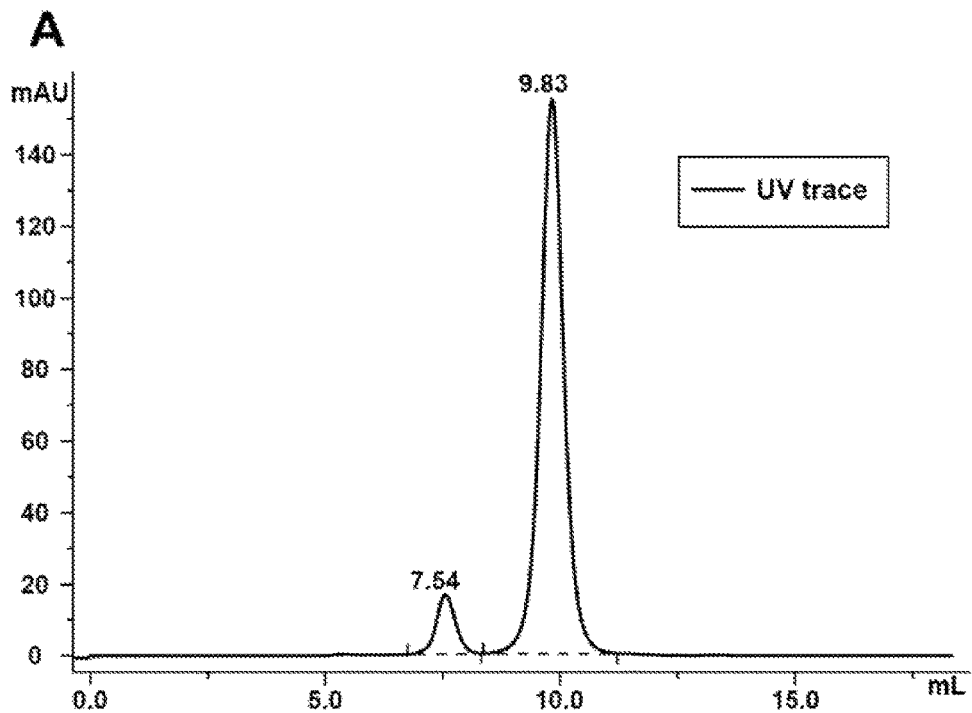
FIGS. 2A-2B show one embodiment of the chromatographic profiles of purified O1 Campos FMDV after incubation at 56° C. for 1 hour and subsequent digestion with Benzonase®.

FIG. 2A shows the chromatographic profiles at U.V. 254 nm of purified O1 Campos FMDV after incubation at 56° C. for 1 hour and subsequent digestion with Benzonase®. Heat treatment at this temperature is known to disassemble the viral particle into 12S particles and/or capsomers and to expose viral RNA to nuclease digestion. Table 3 lists the parameters output from the UV chromatographic analysis of the elution peaks.

TABLE 3

Chromatographic parameters of purified O1 Campos FMDV after heat/enzyme treatment

| Peak | Elution Volume (ml) | Area (mAU * ml) | Height (mAU) |
|---|---|---|---|
| 1 | 7.54 | 2.6846 | 5.946 |
| 2 | 9.83 | 172.3857 | 265.774 |

The chromatographic profile at U.V. 254 nm of purified O1 Campos FMDV after heat/enzyme treatment showed two peaks, a small one at 7.54 mL and a big one at 9.83 mL. The peak observed on the chromatographic profile of the reference O1 Campos sample before treatment (elution volume 6.33 mL on FIG. 1A) has totally disappeared on this chromatographic profile.

Figure 2B:
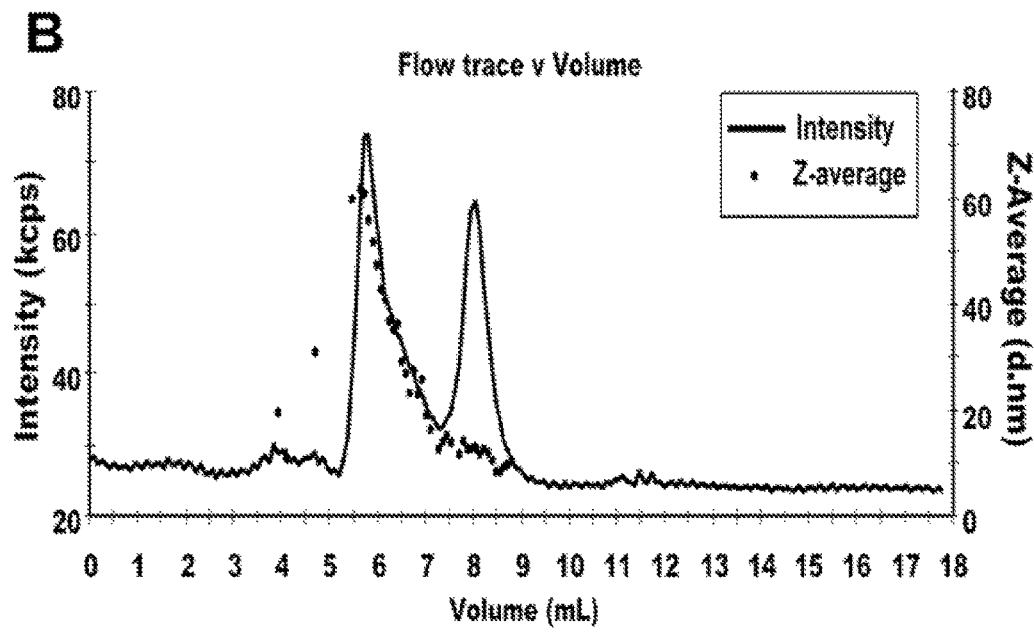

The light scattering intensity trace, as presented in FIG. 2B (solid line) in the DLS detector shows two signals. Table 4 lists the parameters output from the DLS analysis of the elution peaks.

TABLE 4

DLS analysis of purified O1 Campos FMDV after heat/enzyme treatment

| Peak | Start volume (mL) | End volume (mL) | Size (d · nm) | % Int. | DLS SD (d · nm) | Estimated MW (kDa) |
|---|---|---|---|---|---|---|
| 1 | 6.27 | 6.6 | 33.42 | 6.2 | 2.606 | 2450 |
| 2 | 7.21 | 9.48 | 13.03 | 93.8 | 1.371 | 270 |

The first one, between 6.27 mL and 6.6 mL of elution volume, represents only 6.2% of scattered light and did not correlate with significant U.V. detection. The Z-average trace showed for this peak a variable size ranging from 20 to 60 nm with a Z-average of 33.42 nm. As confirmed by the western blot analysis with antibodies against FMDV viral proteins, this peak was produced by the FMD virus particles which were not disintegrated upon treatment (data not shown).

The second intensity peak, with a Z-average diameter of 13.03 nm in the 7.21 to 9.48 mL of elution volume range, correlated with the smaller peak at 7.54 mL in the U.V. 254 nm profile. This peak produced intense signals in western blot analysis (data not shown). Based on size and reactivity, this peak was attributed to FMDV degraded fragments (12S particles and/or capsomers), which were 100% constituted of proteins and therefore displayed low absorption property at 254 nm (denoted by the peak at 7.54 ml in FIG. 2A).

The high peak eluted at 9.83 mL observed in the U.V. chromatography profile (FIG. 2A) was not detected by the DLS detector (FIG. 2B). This result was consistent with the ribonucleotides and/or oligoribonucleotides produced after Benzonase® digestion of the FMDV viral RNA genome.

Example 3

Effect of Chloroform Extraction and Benzonase Digestion on Quantification of a Non-Enveloped Virus Particles in a Viral Concentrate Prepared by PEG Precipitation This example illustrates the usefulness of the combined treatments of nuclease digestion and solvent extraction. In one embodiment, Benzonase® digestion was used to remove the contaminant cellular nucleic acids and chloroform extraction was used to clean up lipid contaminants.

Equipment and Operating Conditions:
Equipment, reagents and solutions used were the same as described in Example 2 except the following differences:
Chromatograph: Äkta Purifier UPC-10 form General Electric with 254/280 nm fixed wavelength UV and conductivity detectors with Unicom control software.
Dilution Buffer for PEG concentrated virus: 30 mM Tris, 100 mM NaCl, pH=8.

Analysis Procedure:
Cell culture supernatant of BHK cells suspension cultures infected with O1 Campos FMDV strain were chemically inactivated and concentrated 50 times (50×) by precipitation by addition of a concentrated solution of PEG 6000, to reach a final PEG concentration of 5.5%. After 72 hours of precipitation, the supernatant is discarded and the 50×FMDV concentrate harvested.

The harvested virus concentrate was subsequently diluted by 10 times with Dilution Buffer 30 mM Tris. 100 mM NaCl, pH=8 and magnetically stirred overnight at 4° C. to reduce the PEG concentration and allow the viral particles to get back into a soluble form.

a) Pre-Treatment of Samples
Four different aliquots of the diluted FMDV concentrate sample were treated before the chromatographic run as follows:
i) 5 mL of chloroform was added to 5 mL of sample and vigorously shaken to thoroughly mix. The mix was centrifuged to break the formed emulsion and the upper aqueous layer was recovered by pipetting.
ii) 2 mL of sample was enzymatically digested with Benzonase® as described in Example 2.
iii) 2 mL of aqueous aliquot recovered from aliquot i). was enzymatically digested with Benzonase® as described in Example 2.
iv) 2 mL of sample was not treated, neither by chloroform extraction nor by enzymatic digestion.

All four aliquots were centrifuged at 16000 g before the chromatographic analysis to eliminate any insoluble material and resulting supernatants were transferred to fresh tubes without disturbing the pellet.

b) Chromatographic Analysis
Chromatographic analysis of all four aliquots was performed as described in Example 2. Injection volume was 100 μL and absorbance was monitored at 254 nm.

Figure 3A:
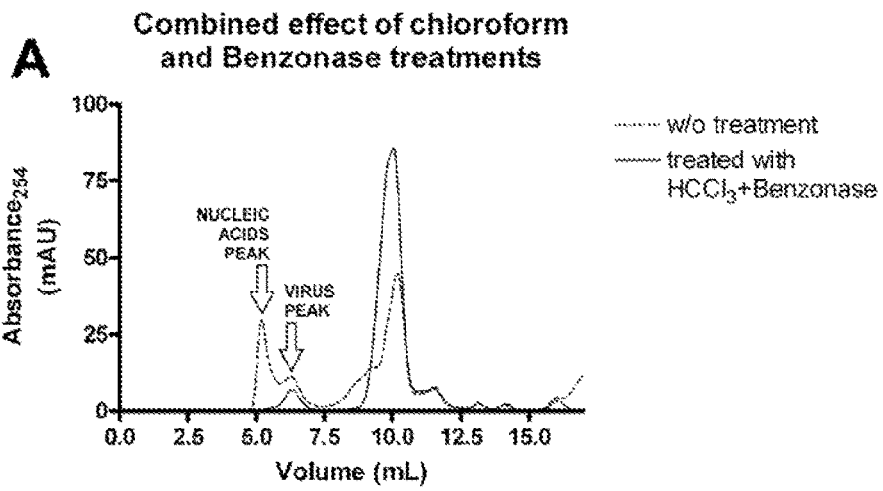
FIGS. 3A-3C show one embodiment of the effect of chloroform extraction and Benzonase® digestion on the quantification of FMDV O1 Campos particles in a viral concentrate prepared by PEG precipitation.
Figure 3B:
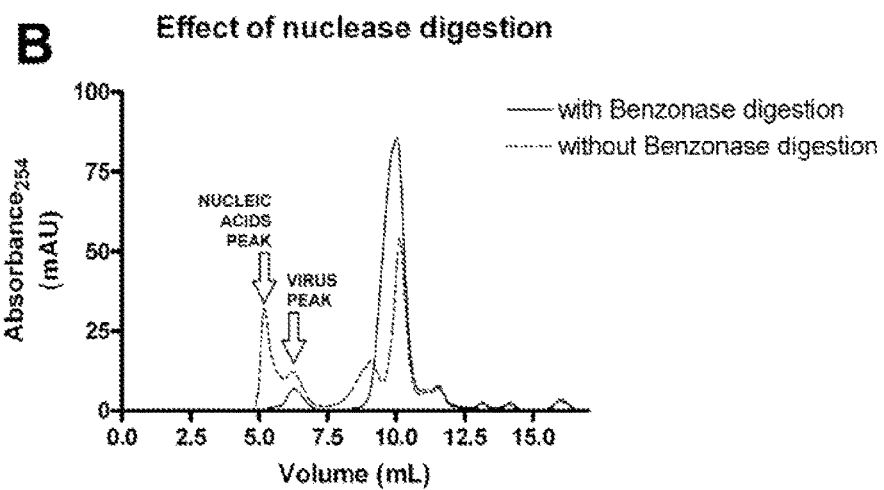
Figure 3C:
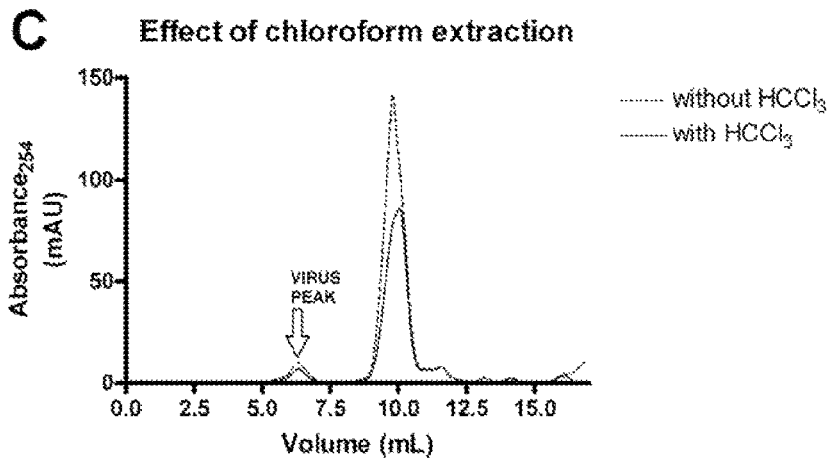

Interpretation of Results
Results are shown in FIG. 3. In FIG. 3A, a comparison was made between untreated and fully treated samples. In the untreated sample, the virus peak was not resolved from nucleic acid peaks and eluted as a "shoulder". In this case, accurate virus peak integration was not possible to achieve due to the nucleic acid contaminants. On the contrary, in the treated sample, the virus peak conformed to a symmetric "Gaussian bell" shaped peak that resolved to baseline. FIG. 3B illustrates the effect of omitting enzymatic treatment on chloroform extracted samples, showing that the main differences in virus peak shape was due to this digestion step. FIG. 3C highlights the point that even after enzymatic digestion, some high molecular weight lipid residues remained at the excluded volume. These lipid contaminants could be eliminated by chloroform extraction. Not performing this step may therefore lead to the overestimation of virus content in the sample.

Example 4

Determination of Stability of Vaccines Containing Enveloped and Non-Enveloped Viruses This example illustrates one embodiment of the present invention for determining stability of a viral vaccine. Vaccines containing viral particles at an initial time and at later times after storage at 4° C. can be analyzed using the method as described herein. U.V. and DLS profiles obtained are analyzed for computing quantity and size of the viral particles. Change in number of viral particles upon storage can be interpreted in terms of percentage of the initial particles. Integrity of the viral particles can also be assessed by comparing the profiles obtained.

Example 5

Quantification and Characterization of Non-Enveloped Virus Particles in High Concentration This example illustrates the application of the present invention to a highly concentrated non-enveloped virus samples obtained by ultrafiltration. In one embodiment, this example illustrates the application of the present invention to a highly concentrated FMDV sample. In another embodiment, this example illustrates the application of the present invention to a concentrated Rotavirus sample.

In one embodiment, this example also illustrates the quantification and the characterization of serial dilutions of FMDV antigens which were prepared from the antigen concentrate obtained by an ultrafiltration process. In another embodiment this example also illustrates the quantification and the characterization of serial dilutions of Rotavirus antigens which were prepared from the antigen concentrate obtained by an ultrafiltration process.

I—Analysis of Highly Concentrated FMDV Samples

Equipment and Operating Conditions:

Equipment used and procedures performed were the same as described in Example 2.

Analysis Procedure:

The infection of the BHK cells by O1 Campos strain in culture in bioreactors produced a low concentration material which was immediately inactivated by chemical inactivation with ethylenimine solution. This O1 Campos viral suspension was then concentrated by an ultrafiltration process in order to reach a high concentration factor of 150×. During the concentration process, concentration and quality of the virus in the sample was closely monitored in order to evaluate the process yields and integrity of the concentrated antigens. The virus concentration of this viral suspension was estimated to be in the range of 700 to 800 µg/mL based on the initial volume of the viral suspension, volume reduction ratios and HPLC determinations along the ultrafiltration process. Three set of serial dilutions were prepared in three different days according to the dilution scheme shown in the Table 5. The three serial viral dilution samples were pre-treated and analyzed with duplicate injection for each sample using the method described in Example 2 using an Agilent 1260 Infinity chromatograph. Samples of both pure FMDV concentrate and dilution buffer were also analyzed. The buffer used for dilution of the sample has the following composition: 300 mM NaCl; 20 mM Tris Base; pH=8.

TABLE 5

Dilution scheme of FMDV concentrate for the preparation of the different FMDV samples.

| Sample | 0 | 1 | 2 | 3 | 4 | 5 |
|---|---|---|---|---|---|---|
| % of FMDV concentrate (by volume) | 0% | 20% | 40% | 60% | 80% | 100% |
| Volume of FMDV concentrate (µL) | 0 | 200 | 400 | 600 | 800 | 1000 |
| Volume of dilution buffer (µL) | 1000 | 800 | 600 | 400 | 200 | 0 |

The resulting U.V. peak areas were analyzed and the FMD virus particles concentration was deduced for each sample. Duplicate injection results were averaged for each set of serial dilution. The viral concentrations determined were plotted against percent concentration. The final average of the three series was used to perform the regression analysis. Dynamic light scattering data was continuously captured using a Malvern Nano S DLS instrument connected in-line with the HPLC at a sampling frequency of one reading every 10 seconds. Readings corresponding to the virus peak were singled out for Z-average diameter analysis in the Malvern Zetasizer software v. 7.02.

Figure 4A:
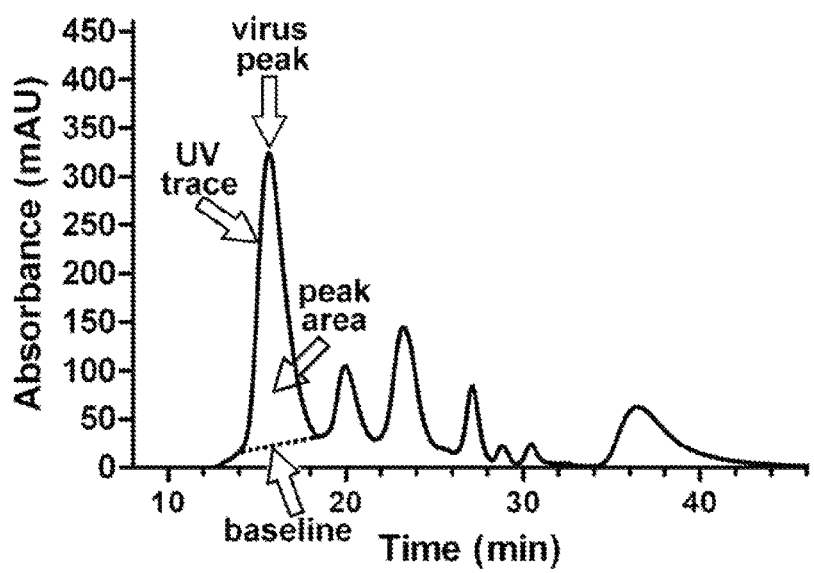
Figure 4B:
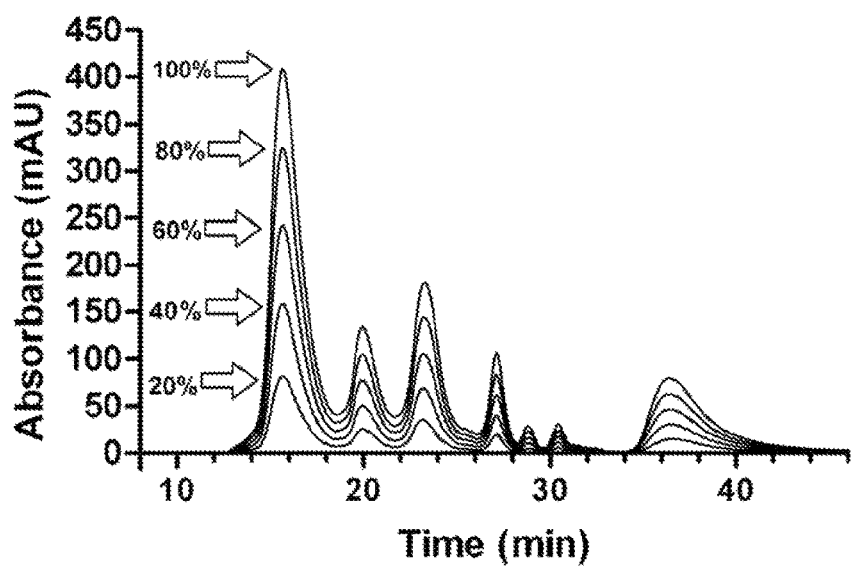
Figure 5A:
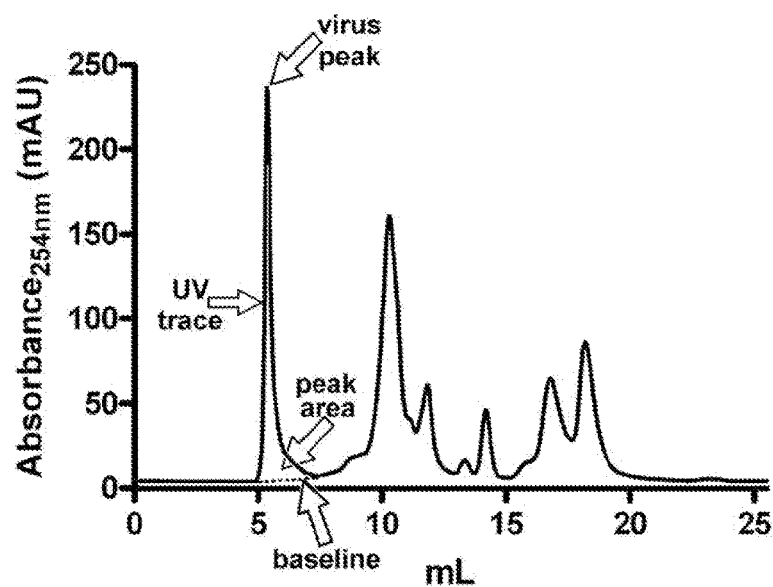
FIGS. 5A-5D show one embodiment of the quantification of a serial dilution of Bovine Rotavirus serotype G6 antigens which were prepared from an antigen concentrate obtained by an ultrafiltration concentration (UF).
Figure 5B:
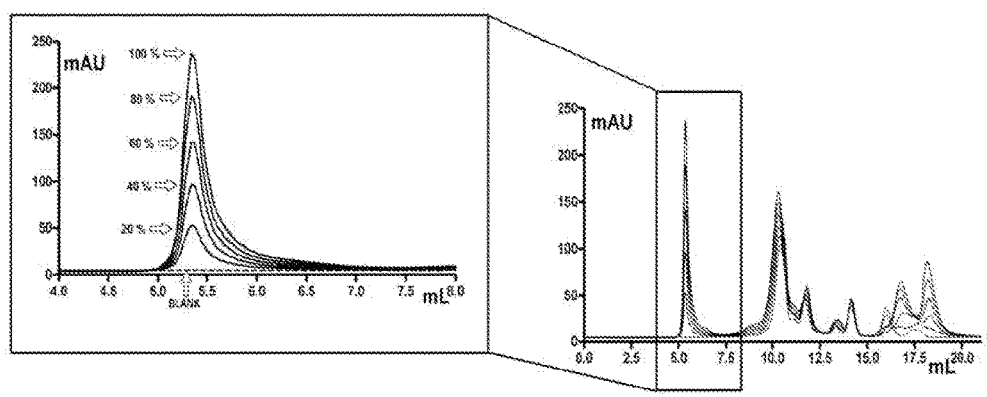
Figure 5C:
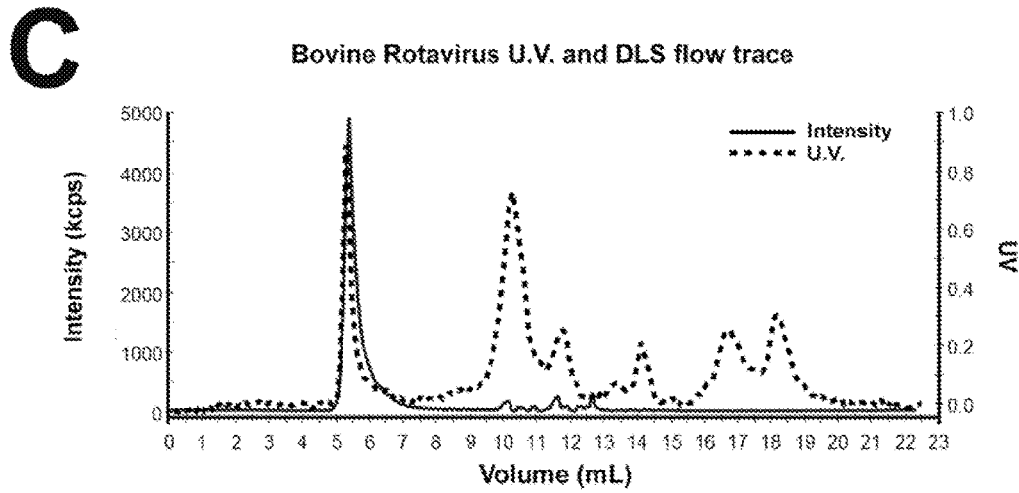
Figure 5D:
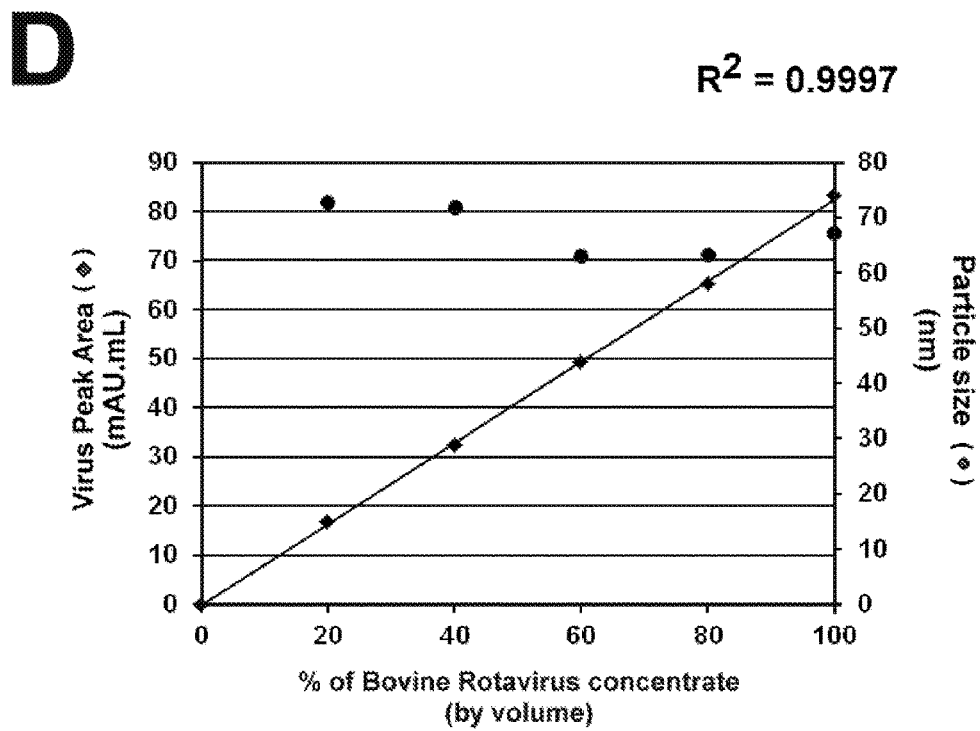

Results:

FIG. 4A shows the chromatographic profile tracked under 254 nm of a FMDV antigen concentrate obtained by the ultrafiltration. FIG. 4B shows the overlay of chromatographic profiles obtained from the five tested FMDV samples ranging from 20% to 100% of FMDV concentrate. FIG. 4C shows the overlay of the UV 254 nm chromatographic profile and the DLS chromatographic profile for one of the sample. The overlay of the U.V. and the DLS profiles clearly shows that the identified FMD virus peak tracked by U.V. is the only peak generating a significant intensity of dispersed light when tracked by DLS. This result indicates that the FMD viral particles in this sample are the only species of molecules big enough to actually disperse the light at an intensity high enough to be detected by the DLS detector.

As indicated in FIG. 4D, a very high coefficient of determination $R^2$ (0.9984) was obtained showing a constant and robust association between the estimated viral concentration and the actual viral concentration of the sample, suggesting that the present invention can accurately estimate the viral concentration over a broad range of viral concentration.

In-line DLS particle size determinations showed constant readings ranging from 29.9 to 34.2 nm and consistent with FMDV particle across all the concentration range assessed (see FIG. 4D and Table 6). All the results obtained from ultraviolet and DLS traces are summarized in Table 6.

TABLE 6

Ultraviolet and DLS analysis of the three sets of FMDV concentrate serial dilution sample

| % FMDV concentrate by volume | $1^{st}$ serial dilution average (µg/mL) | $2^{nd}$ serial dilution average (µg/mL) | $3^{rd}$ serial dilution average (µg/mL) | Final average (µg/mL) | Z-average diameter (nm) |
|---|---|---|---|---|---|
| 0% | 0.0 | 0.0 | 0.0 | 0.0 | / |
| 20% | 145.3 | 131.8 | 133.2 | 136.8 | 32.0 |
| 40% | 283.0 | 273.6 | 273.9 | 276.8 | 32.7 |
| 60% | 433.7 | 432.7 | 424.9 | 430.4 | 34.2 |
| 80% | 581.0 | 629.2 | 600.2 | 603.5 | 29.9 |
| 100% | 730.4 | 761.3 | 689.3 | 727.0 | 31.6 |

II—Analysis of Concentrated Bovine Rotavirus Serotype G6 Samples.

Equipment used and procedures performed were the same as described in Example 2 except the following differences:

Equipment and Operating Conditions:

Chromatographic equipment: a General Electric Healthcare Äkta Purifier UPC-10 chromatograph equipped with binary pump, 254/280 nm fixed wavelength UV detector, conductivity detector and Unicom control and data acquisition software was used.

Chromatography column: TOSOH Bioscience TSKgel G4000PWXL (7.8 mm ID×30.0 cm L) or equivalent was used without guard column or cartridge.

Eppendorf Thermomixer Interchangeable block suitable for different centrifuge tubes.

TURBO™ DNase (2 U/μL), catalog # AM2238; Life Technologies.

TURBO™ DNase 10× buffer, as supplied by the manufacturer: Life Technologies.

Malvern Zetasizer Nano S Dynamic Light Scattering (DLS) ZEN1600 analyzer was controlled and data analyzed with Zetasizer v. 7.11 software.

Analysis Procedure:

A culture of MA104 cells from kidney of green african monkey (Cercophitecus aethiops) were infected with Bovine Rotavirus serotype G6. The cell culture supernatant was inactivated with formaldehyde solution and concentrated by ultrafiltration to reach a 13.4× concentration factor. A placebo solution (negative control) was prepared by repeatedly freezing and thawing of a cell culture.

Sample Dilution:

A serial dilution of the sample was prepared using the placebo as diluent.

TABLE 7

Dilution scheme of Bovine Rotavirus G6 concentrate for the preparation of the different Rotavirus samples.

| Sample | 1 | 2 | 3 | 4 | 5 | 6 |
|---|---|---|---|---|---|---|
| % of concentrate (by volume) | 0% | 20% | 40% | 60% | 80% | 100% |
| Volume of Rotavirus concentrate (mL) | 0 | 1 | 2 | 3 | 4 | 5 |
| Volume of placebo solution (mL) | 5 | 4 | 3 | 2 | 1 | 0 |

Sample Pre-Treatment:

a) Chloroform Extraction:

i) Sample dilutions from previous step were extracted with chloroform as described in Example 3 a) (i), and the aqueous upper layer was recovered.

b) Enzymatic Digestion:

i) To 4.5 mL of each sample obtained in the previous step 500 μL of TURBO™ DNase 10× buffer and 5 μL of TURBO™ DNase (2 U/μL) were added.

ii) A 60 minutes incubation at 37° C. and 750 rpm was performed using the Eppendorf Thermomixer with a thermoblock suitable for 15 mL tubes.

iii) 1 mL of each sample was transferred to a 1.5 mL Eppendorf microcentrifuge tube and centrifuged at 16000 g at 4° C. for 10 minutes. Supernatant was transferred by pipetting to a fresh tube taking care of not to disturb the pellet to avoid clogging the chromatographic column.

Chromatographic Run:

i) 100 μL of each centrifuged, digested sample were injected using a measuring loop in an automatic injection valve.

ii) An isocratic run in GPC1 mobile phase was carried out at a constant flow of 0.5 mL/min monitoring at 254 nm in the U.V detector to obtain the U.V. profile and with the Malvern Zetasizer detector in a serial configuration to acquire the DLS scattered light intensity and Z-average.

iii) U.V. profile was captured and analized using the Unicorn software and scattered light intensity and Z-average of particle diameter were collected and analyzed with the Malvern Zetasizer v. 7.11 software.

Results:

FIG. 5A shows the chromatographic profile tracked under 254 nm of a Bovine Rotavirus antigen concentrate obtained by the ultrafiltration. FIG. 5B shows the overlay of chromatographic profiles obtained from the five tested Rotavirus samples ranging from 20% to 100% of Rotavirus concentrate.

FIG. 5C shows the overlay of the UV 254 nm chromatographic profile and the DLS chromatographic profile for one of the samples. The overlay of the U.V. and the DLS profiles clearly shows that the identified Rotavirus peak tracked by U.V. is the only peak generating a significant intensity of dispersed light when tracked by DLS. This result indicates that the Rotavirus viral particles in this sample are the only species of molecules big enough to actually disperse the light at an intensity high enough to be detected by the DLS detector.

As indicated in FIG. 5D, a very high coefficient of determination $R^2$ (0.9997) was obtained showing a constant and robust association between the estimated viral concentration and the actual viral concentration of the sample, suggesting that the present invention can accurately estimate the Rotavirus particles concentration over a broad range of viral concentration.

In-line DLS particle size determinations showed constant readings ranging from 63.2 to 72.8 nm and consistent with Rotavirus particle across all the concentration range assessed (see FIG. 5D and Table 8). All the results obtained from ultraviolet and DLS traces are summarized in Table 8.

TABLE 8

Ultraviolet and DLS analysis of a Rotavirus concentrate and its serial dilution samples.

| % virus concentrate (by volume) | Peak area (mAU · mL) | Corrected peak area (mAU · mL) | Particle size (nm) |
|---|---|---|---|
| 0 | 0.00 | 0.00 | — |
| 20 | 16.96 | 16.96 | 72.8 |
| 40 | 32.55 | 32.55 | 71.9 |
| 60 | 49.17 | 49.17 | 63.2 |
| 80 | 65.26 | 65.26 | 63.4 |
| 100 | 83.26 | 83.26 | 67.3 |

III—Interpretation of Results.

This example illustrates that the present application is capable of generating accurate measurement over a broad range of viral concentrations for non-enveloped viruses.

In one embodiment, this example shows that the present application is capable of generating accurate measurement for viral particles such as FMDV and Bovine Rotavirus over a broad range of viral concentrations as indicated by the high linearity of viral concentration determined from various viral samples diluted from a high viral concentrate.

This example shows the capability of the present invention to consistently and accurately characterize the size of FMDV or Bovine Rotavirus antigen and integrity independent of the viral concentration.

This example demonstrates that the present invention can be used with great accuracy to quantify the viral concentration from low concentration infection supernatant to high concentrates of FMDV particles, up to 150× and 727 μg/mL as tested in this example. In addition, in-line DLS detection is shown to be capable of characterizing the viral particle size and integrity with great accuracy and consistency across the full range of concentration of viral particles. This feature is particularly important during this type of concentration process as certain variable conditions of the process, like temperature, pH and the shear rate used could have dramatic impact on the viral particles integrity. Thus the present invention represents the ultimate tool of Process Analytical Technology (PAT) to ensure the success of the concentration step of the manufacturing process and to guarantee the quality of the concentrated antigen produced, no matter how high the final concentration is.

Based on spectrophotometric error considerations it can be reasonably anticipated that concentrations that are two or three times as high as the one measured in this experiment can be accurately quantified with the present method, reaching for FMDV particles the upper range of about 2250 µg/mL. This is based on the fact that photometric errors are quite low in the range of 100 mAU to 1500 mAU. It is also possible to inject a smaller sample volume, e.g. 50 µL instead of 100 µL or simply dilute the sample according to the anticipated concentration and correct the obtained result by the dilution factor. Accordingly, the present method can work on a concentration range that is well beyond the need of any practical manufacturing processes.

Dynamic Light Scattering detectors routinely work with protein samples in the order of 2 mg/mL or higher. So there is no doubt that the in-line DLS detection method described in the present invention would work perfectly well with samples with a higher concentration as the one describe in this example.

Typical concentration steps in FMD vaccine manufacturing processes reach concentrations that range from 10× to 60× of the virus concentration obtained during the infection step in cell culture. Nevertheless, when the objective is to produce a very highly concentrated FMD viral antigen bank, the concentration step can be continued until reaching concentration factor of 150× and even 200×. In this example, the highly concentrated virus material with a measured concentration of 727 µg/mL corresponds to a concentration factor of 150×. Although the upper limit for the concentration factor has to be determined case by case for each FMDV viral strain, it can be reasonably estimated that concentration of FMDV antigens up to 1250 µg/mL (or 1.25 mg/mL) or higher could be reached without causing negative impact on the solubility of the FMDV particles.

As demonstrated in this example, the method of the present invention is well suited to quantify and characterize non-enveloped viral particles in very highly concentrated samples and therefore can be applied to ultraconcentrated FMDV antigen banks or Bovine Rotavirus antigen banks.

As a reference, usual virus concentration in vaccines varies according to virus strains, national regulatory agencies requirements and pharmacotechnical properties of the vaccine. The most common types of FMD vaccines are water-in-oil emulsions or water-in-oil-in-water double emulsions. The aqueous phases used to prepare the emulsions range in virus concentration from about 2 µg/mL to 60 µg/mL.

Example 6

Quantification and Characterization of Enveloped Virus Particles in High Concentration This example illustrates the application of the present invention to concentrated enveloped virus samples obtained by ultrafiltration. In one embodiment, this example illustrates the application of the present invention to a concentrated BoHV-5 sample. In another embodiment, this example illustrates the application of the present invention to a concentrated PIV-3 sample. In another embodiment, this example illustrates the application of the present invention to a concentrated Rabies virus sample In one embodiment, this example also illustrates the quantification and the characterization of serial dilutions of BoHV-5 antigens, PIV-3 antigens and Rabies virus antigens which were prepared from the antigen concentrate obtained by an ultrafiltration process.

I) Analysis of Concentrated BoHV-5 Samples

Equipment used and procedures performed were the same as described in Example 2 with the following differences:

Equipment and Operating Conditions:

Chromatographic equipment: a General Electric Healthcare Äkta Purifier UPC-10 chromatograph equipped with binary pump, 254/280 nm fixed wavelength UV detector, conductivity detector and Unicorn control and data acquisition software was used.

Chromatography column: General Electric Healthcare XK 16/40 borosilicate glass column (16 mm ID×40.0 cm L) packed according to instructions from the manufacturer with GE Healtcare Life Sciences Sephacryl S-400 SEC/GPC chromatographic media.

Eppendorf Thermomixer Interchangeable block suitable for different centrifuge tubes.

TURBO™ DNase (2 U/µL), catalog # AM2238: Life Technologies.

TURBO™ DNase 10× buffer, as supplied by the manufacturer; Life Technologies.

Malvern Zetasizer Nano S Dynamic Light Scattering (DLS) ZEN1600 analyzer was controlled and data analyzed with Zetasizer v. 7.11 software.

Analysis Procedure:

A culture of Madin-Darby bovine kidney cells (MDBK) were infected with Bovine Herpesvirus 5 (BoHV-5) strain A663, the cell culture supernatant was inactivated with ethylenimine solution and concentrated by ultrafiltration to reach a 6.4× concentration factor. A placebo solution (negative control) was prepared by repeatedly freezing and thawing of a cell culture.

Sample Dilution:

A serial dilution of the sample was prepared using the placebo as diluent.

TABLE 9

Dilution scheme of BoHV-5 concentrate for the preparation of the different BoHV-5 samples

| Sample | 1 | 2 | 3 | 4 | 5 | 6 |
|---|---|---|---|---|---|---|
| % of concentrate (by volume) | 0% | 20% | 40% | 60% | 80% | 100% |
| Volume of BoHV-5 concentrate (mL) | 0 | 1 | 2 | 3 | 4 | 5 |
| Volume of placebo Solution (mL) | 5 | 4 | 3 | 2 | 1 | 0 |

Sample Pre-Treatment:
 a) Enzymatic Digestion:
  i) To 4.5 mL of each diluted sample 500 µL of TURBO™ DNase 10× buffer and 20 µL of TURBO™ DNase (2 U/µL) were added.
  ii) A 60 minutes incubation at 37° C. and 750 rpm was performed using the Eppendorf Thermomixer with a thermoblock suitable for 15 mL tubes.
  iii) 1 mL of each sample was transferred to a 1.5 mL Eppendorf microcentrifuge tube and centrifuged at 16000 g at 4° C. for 10 minutes. Supernatant was transferred by pipetting to a fresh tube taking care of not to disturb the pellet to avoid clogging the chromatographic column.

Chromatographic Run:
- i) 940 μL of each centrifuged, digested sample were injected using a measuring loop in an automatic injection valve.
- ii) An isocratic run in GPC1 mobile phase was carried out at a constant flow of 1 mL/min monitoring at 254 nm in the U.V detector to obtain the U.V. profile and with the Malvern Zetasizer detector in a serial configuration to acquire the DLS scattered light intensity and Z-average.
- iii) U.V. profile was captured and analyzed using the Unicorn software and scattered light intensity and Z-average of particle diameter were collected and analyzed with the Malvern Zetasizer v. 7.11 software.

Figure 6A:
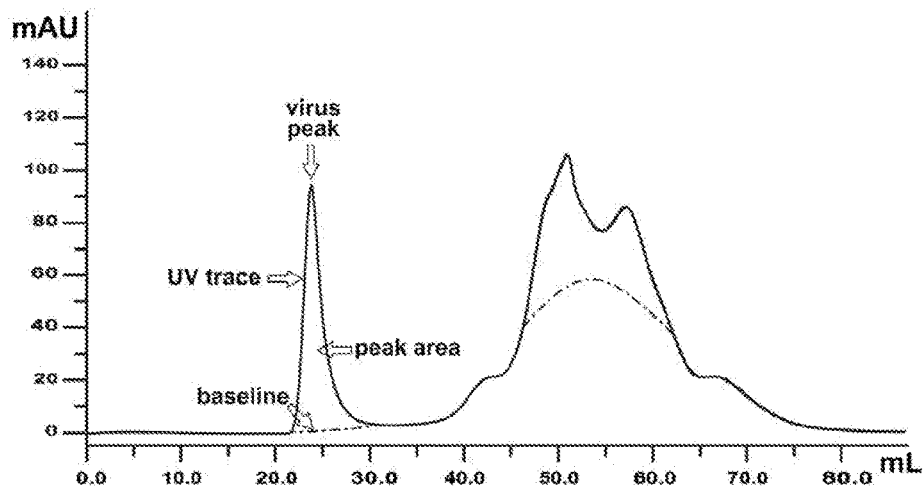
Figure 6B:
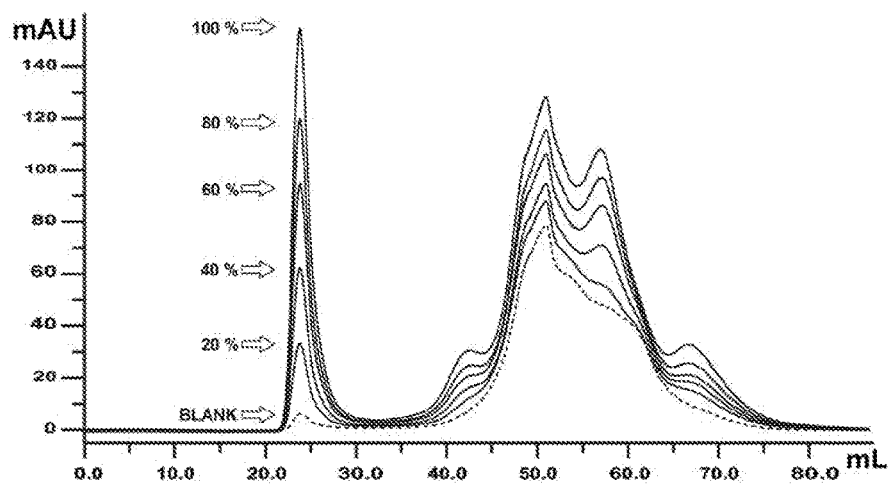
Figure 7A:
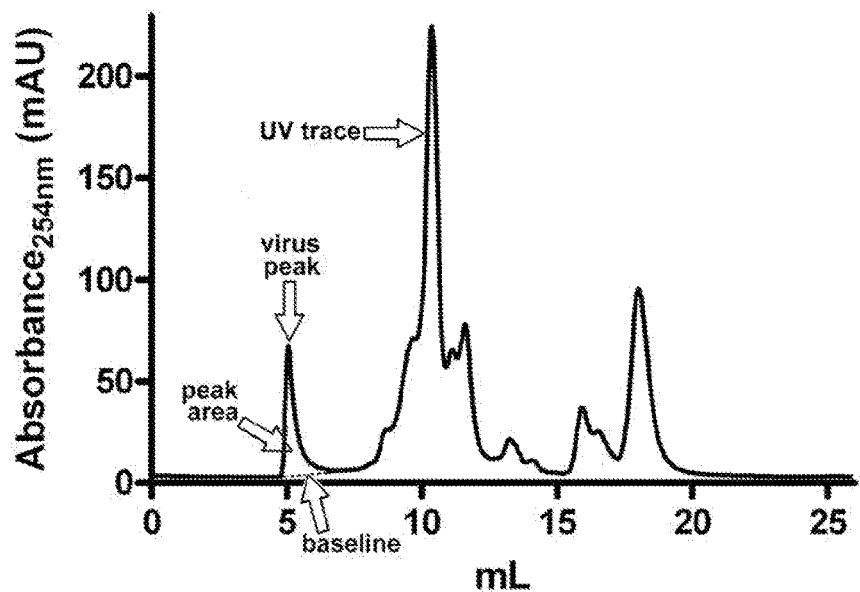
FIGS. 7A-7D show one embodiment of the quantification of a serial dilution of PIV-3 antigens which were prepared from an antigen concentrate obtained by an ultrafiltration concentration (UF).
Figure 7B:
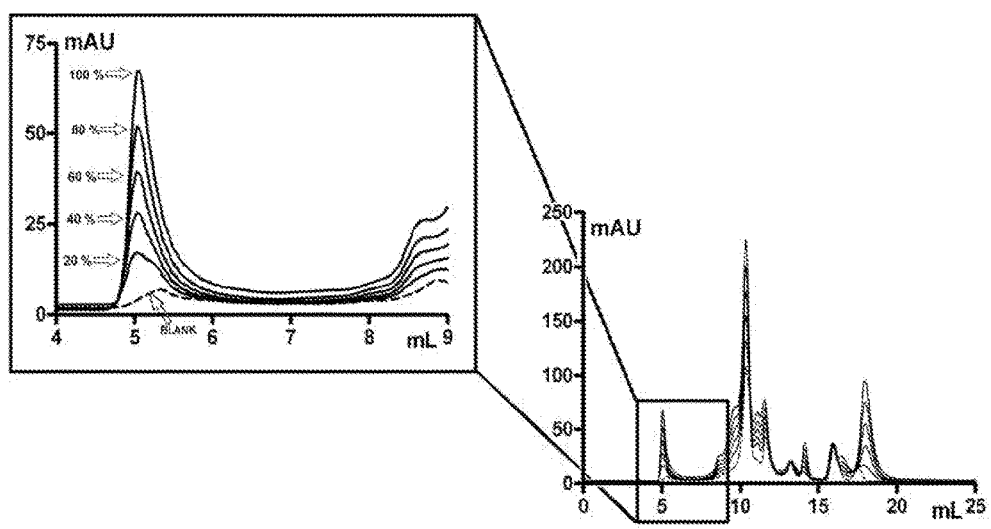

Results:

FIG. 6A shows the chromatographic profile tracked under 254 nm of a BoHV-5 antigen concentrate obtained by the ultrafiltration. FIG. 6B shows the overlay of chromatographic profiles obtained from the five tested BoHV-5 samples ranging from 20% to 100% of BoHV-5 concentrate.

FIG. 6C shows the overlay of the UV 254 nm chromatographic profile and the DLS chromatographic profile for one of the samples. The overlay of the U.V. and the DLS profiles clearly shows that the identified BoHV-5 peak tracked by U.V. is the only peak generating a significant intensity of dispersed light when tracked by DLS. This result indicates that the BoHV-5 viral particles in this sample are the only species of molecules big enough to actually disperse the light at an intensity high enough to be detected by the DLS detector.

As indicated in FIG. 6D, a very high coefficient of determination $R^2$ (0.9987) was obtained showing a constant and robust association between the estimated viral concentration and the actual viral concentration of the sample, suggesting that the present invention can accurately estimate the BoHV-5 particles concentration over a broad range of viral concentration.

In-line DLS particle size determinations showed constant readings ranging from 137.1 to 151.7 nm and consistent with BoHV-5 particle across all the concentration range assessed (see FIG. 6D and Table 10). All the results obtained from ultraviolet and DLS traces are summarized in Table 10.

TABLE 10

Ultraviolet and DLS analysis of a BoHV-5 concentrate and its serial dilution samples

| % virus concentrate (by volume) | Peak area (mAU · mL) | Corrected peak area (mAU · mL) | Particle size (nm) |
|---|---|---|---|
| 0 | 13.83 | 0.00 | / |
| 20 | 77.49 | 63.66 | 151.7 |
| 40 | 143.64 | 129.81 | 149.1 |
| 60 | 221.29 | 207.46 | 143.2 |
| 80 | 280.50 | 266.68 | 141.4 |
| 100 | 356.99 | 343.16 | 137.1 |

Analysis of Concentrated PIV-3 Samples

Equipment used and procedures performed were the same as described in Example 2 with the following differences:

Equipment and Operating Conditions:

Chromatographic equipment: a General Electric Healthcare Äkta Purifier UPC-10 chromatograph equipped with binary pump, 254/280 nm fixed wavelength UV detector, conductivity detector and Unicorn control and data acquisition software was used.

Chromatography column: TOSOH Bioscience TSKgel G4000PWXL (7.8 mm ID×30.0 cm L) or equivalent was used without guard column or cartridge.

Eppendorf Thermomixer Interchangeable block suitable for different centrifuge tubes.

TURBO™ DNase (2 U/μL), catalog # AM2238; Life Technologies.

TURBO™ DNase 10× buffer, as supplied by the manufacturer; Life Technologies.

Malvern Zetasizer Nano S Dynamic Light Scattering (DLS) ZEN1600 analyzer was controlled and data analyzed with Zetasizer v. 7.11 software.

Analysis Procedure:

A culture of Madin-Darby bovine kidney cells (MDBK) were infected with Parainfluenza Virus 3 (PIV-3), the cell culture supernatant was inactivated with ethylenimine solution and concentrated by ultrafiltration to reach a 19.4× concentration factor. A placebo solution (negative control) was prepared by repeatedly freezing and thawing of a cell culture.

Sample Dilution:

A serial dilution of the sample was prepared using the placebo as diluent.

TABLE 11

Dilution scheme of PIV-3 concentrate for the preparation of the different PIV-3 samples

| Sample | 1 | 2 | 3 | 4 | 5 | 6 |
|---|---|---|---|---|---|---|
| % of concentrate (by volume) | 0% | 20% | 40% | 60% | 80% | 100% |
| Volume of PIV-3 concentrate (mL) | 0 | 1 | 2 | 3 | 4 | 5 |
| Volume of placebo solution (mL) | 5 | 4 | 3 | 2 | 1 | 0 |

Sample Pre-Treatment:

a) Enzymatic Digestion:

i) To 4.5 mL of each sample obtained in the previous step 500 μL of TURBO™ DNase 10× buffer and 5 μL of TURBO™ DNase (2 U/μL) were added.

ii) A 60 minutes incubation at 37° C. and 750 rpm was performed using the Eppendorf Thermomixer with a thermoblock suitable for 15 mL tubes.

iii) 1 mL of each sample was transferred to a 1.5 mL Eppendorf microcentrifuge tube and centrifuged at 16000 g at 4° C. for 10 minutes. Supernatant was transferred by pipetting to a fresh tube taking care of not to disturb the pellet to avoid clogging the chromatographic column.

Chromatographic Run:

i) 100 μL of each centrifuged, digested sample were injected using a measuring loop in an automatic injection valve.

ii) An isocratic run in GPC1 mobile phase was carried out at a constant flow of 0.5 mL/min monitoring at 254 nm in the U.V detector to obtain the U.V. profile and with the Malvern Zetasizer detector in a serial configuration to acquire the DLS scattered light intensity and Z-average.

iii) U.V. profile was captured and analyzed using the Unicorn software and scattered light intensity and Z-average of particle diameter were collected and analyzed with the Malvern Zetasizer v. 7.11 software.

Results:

FIG. 7A shows the chromatographic profile tracked under 254 nm of a PIV-3 antigen concentrate obtained by the ultrafiltration. FIG. 7B shows the overlay of chromatographic profiles obtained from the five tested PIV-3 samples ranging from 20% to 100% of PIV-3 concentrate.

Figure 7C:
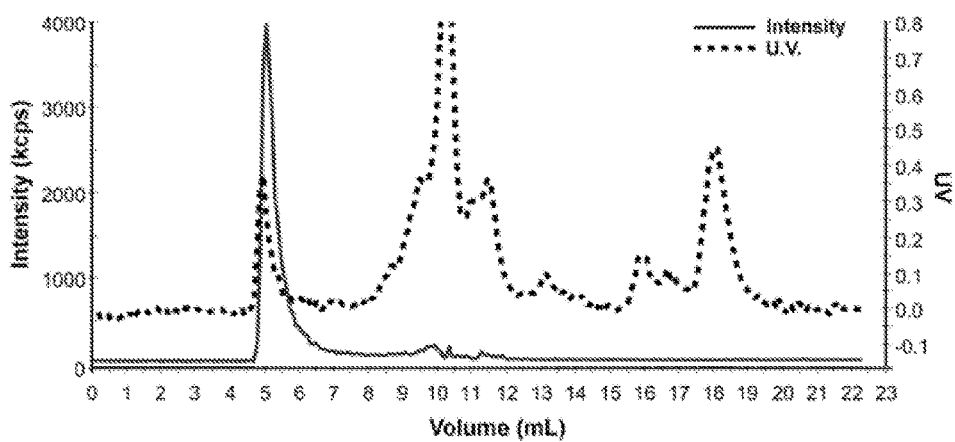

FIG. 7C shows the overlay of the UV 254 nm chromatographic profile and the DLS chromatographic profile for one of the sample. The overlay of the U.V. and the DLS profiles clearly shows that the identified PIV-3 peak tracked by U.V. is the only peak generating a significant intensity of dispersed light when tracked by DLS. This result indicates that the PIV-3 viral particles in this sample are the only species of molecules big enough to actually disperse the light at an intensity high enough to be detected by the DLS detector.

Figure 7D:
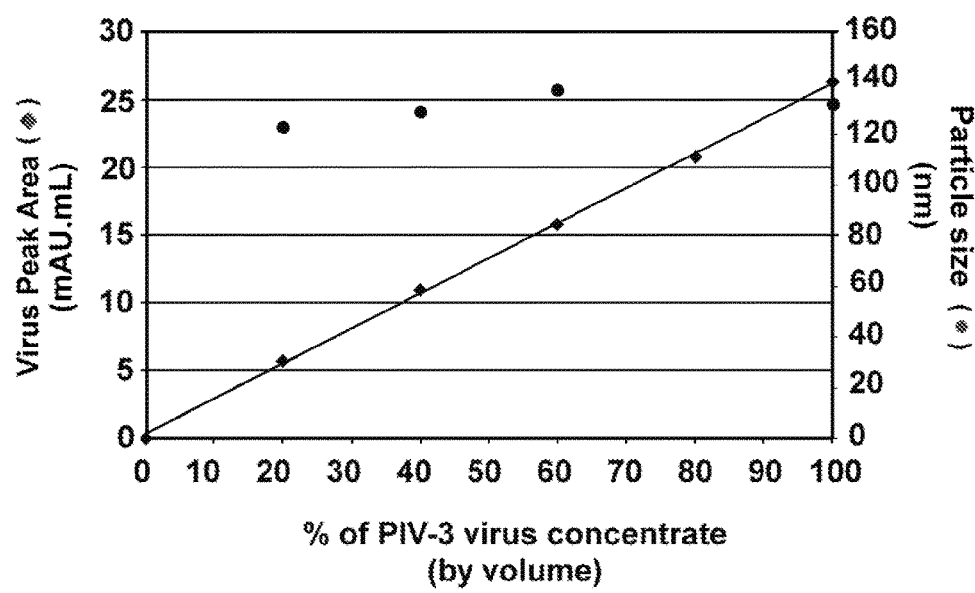

As indicated in FIG. 7D, a very high coefficient of determination $R^2$ (0.9993) was obtained showing a constant and robust association between the estimated viral concentration and the actual viral concentration of the sample, suggesting that the present invention can accurately estimate the PIV-3 particles concentration over a broad range of viral concentration.

In-line DLS particle size determinations showed constant readings ranging from 123 to 138 nm and consistent with PIV-3 particle across all the concentration range assessed (see FIG. 7D and Table 12). For one of the sample analyzed (80% of virus concentrate), the DLS signal failed to register so the z-average size reading could not be performed. All the results obtained from ultraviolet and DLS traces are summarized in Table 12.

TABLE 12

Ultraviolet and DLS analysis of a PIV-3 concentrate and its serial dilution samples

| % virus concentrate (by volume) | Peak area (mAU · mL) | Corrected peak area (mAU · mL) | Particle size (nm) |
|---|---|---|---|
| 0 | 3.17 | 0 | — |
| 20 | 8.92 | 5.75 | 123 |
| 40 | 14.19 | 11.02 | 129 |
| 60 | 19.03 | 15.86 | 138 |
| 80 | 24.04 | 20.86 | — |
| 100 | 29.54 | 26.37 | 132 |

III) Analysis of Concentrated Rabies Virus Samples.

Equipment used and procedures performed were the same as described in Example 2 with the following differences:

Equipment and Operating Conditions:
  Chromatographic equipment: a General Electric Healthcare Äkta Purifier UPC-10 chromatograph equipped with binary pump, 254/280 nm fixed wavelength UV detector, conductivity detector and Unicorn control and data acquisition software was used.
  Chromatography column: TOSOH Bioscience TSKgel G4000PWXL (7.8 mm ID×30.0 cm L) or equivalent was used without guard column or cartridge.
  Eppendorf Thermomixer Interchangeable block suitable for different centrifuge tubes.
  TURBO™ DNase (2 U/μL), catalog # AM2238; Life Technologies.
  TURBO™ DNase 10x buffer, as supplied by the manufacturer; Life Technologies.
  Malvern Zetasizer Nano S Dynamic Light Scattering (DLS) ZEN1600 analyzer was controlled and data analyzed with Zetasizer v. 7.11 software.

Analysis Procedure:

A culture of Baby Hamster Kidney cells (BHK21) were infected with Rabies virus (strain Pasteur vaccins/PV)), the cell culture supernatant was inactivated with ethylenimine solution and concentrated by ultrafiltration in order to reach a 10.2× concentration factor. A placebo solution (negative control) was prepared by collecting a non-infected cell culture of the same growing age of the infected cultures at harvest time.

Sample Dilution:

A serial dilution of the sample was prepared using the placebo as diluent.

TABLE 13

Dilution scheme of Rabies virus concentrate for the preparation of the different Rabies virus samples

| Sample | 1 | 2 | 3 | 4 | 5 | 6 |
|---|---|---|---|---|---|---|
| % of concentrate (by volume) | 0% | 20% | 40% | 60% | 80% | 100% |
| Volume of Rabies PV concentrate (mL) | 0 | 1 | 2 | 3 | 4 | 5 |
| Volume of Placebo solution (mL) | 5 | 4 | 3 | 2 | 1 | 0 |

Sample Pre-Treatment:

a) Enzymatic Digestion:

i) To 4.5 mL of each sample obtained in the previous step 500 μL of TURBO™ DNase 10× buffer and 5 μL of TURBO™ DNase (2 U/μL) were added.

ii) A 60 minutes incubation at 37° C. and 750 rpm was performed using the Eppendorf Thermomixer with a thermoblock suitable for 15 mL tubes.

iii) 1 mL of each sample was transferred to a 1.5 mL Eppendorf microcentrifuge tube and centrifuged at 16000 g at 4° C. for 10 minutes. Supernatant was transferred by pipetting to a fresh tube taking care of not to disturb the pellet to avoid clogging the chromatographic column.

Chromatographic Run:

i) 100 μL of each centrifuged, digested sample were injected using a measuring loop in an automatic injection valve.

ii) An isocratic run in GPC1 mobile phase was carried out at a constant flow of 0.5 mL/min monitoring at 254 nm in the U.V detector to obtain the U.V. profile and with the Malvern Zetasizer detector in a serial configuration to acquire the DLS scattered light intensity and Z-average.

iii) U.V. profile was captured and analized using the Unicorn software and scattered light intensity and Z-average of particle diameter were collected and analyzed with the Malvern Zetasizer v. 7.11 software.

Results:

FIG. 8A shows the chromatographic profile tracked under 254 nm of a Rabies virus antigen concentrate obtained by the ultrafiltration. FIG. 8B shows the overlay of chromatographic profiles obtained from the five tested Rabies virus samples ranging from 20% to 100% of Rabies virus concentrate.

FIG. 8C shows the overlay of the UV 254 nm chromatographic profile and the DLS chromatographic profile for one of the sample. The overlay of the U.V. and the DLS profiles clearly shows that the identified Rabies virus peak tracked by U.V. is the only peak generating a significant intensity of dispersed light when tracked by DLS. This result indicates that the Rabies viral particles in this sample are the only species of molecules big enough to actually disperse the light at an intensity high enough to be detected by the DLS detector.

Figure 8A:
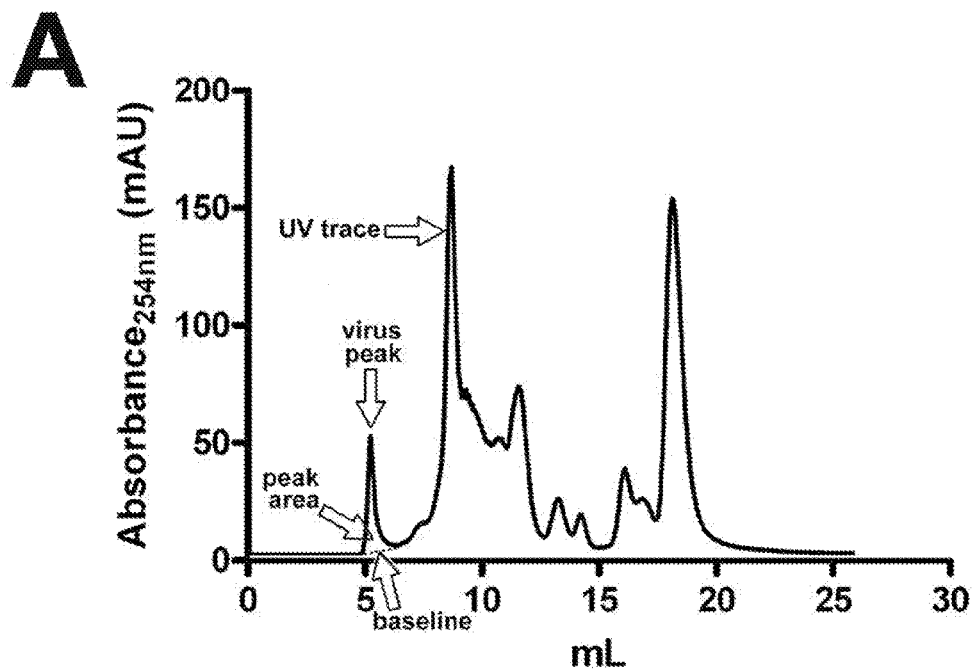
FIGS. 8A-8D show one embodiment of the quantification of a serial dilution of Rabies virus antigens which were prepared from an antigen concentrate obtained by an ultrafiltration concentration (UF).
Figure 8B:
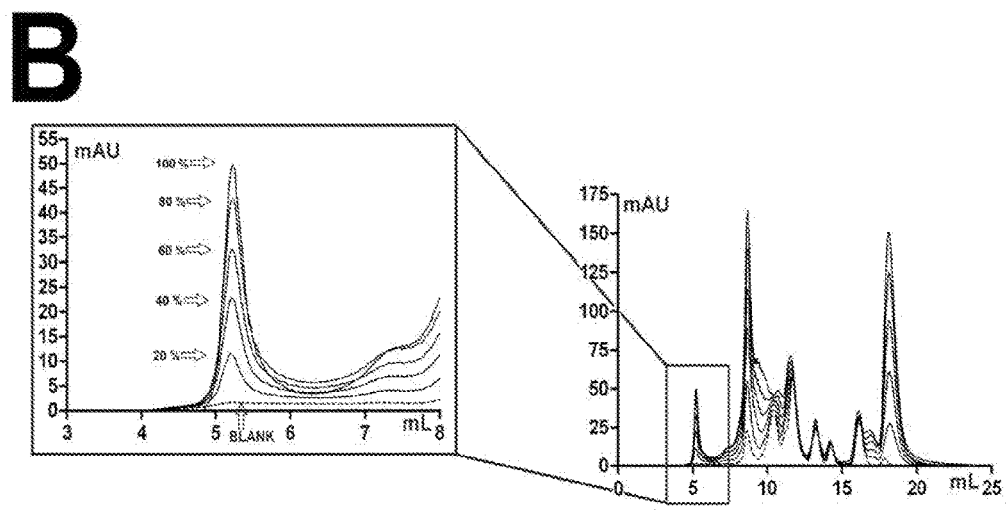
Figure 8C:
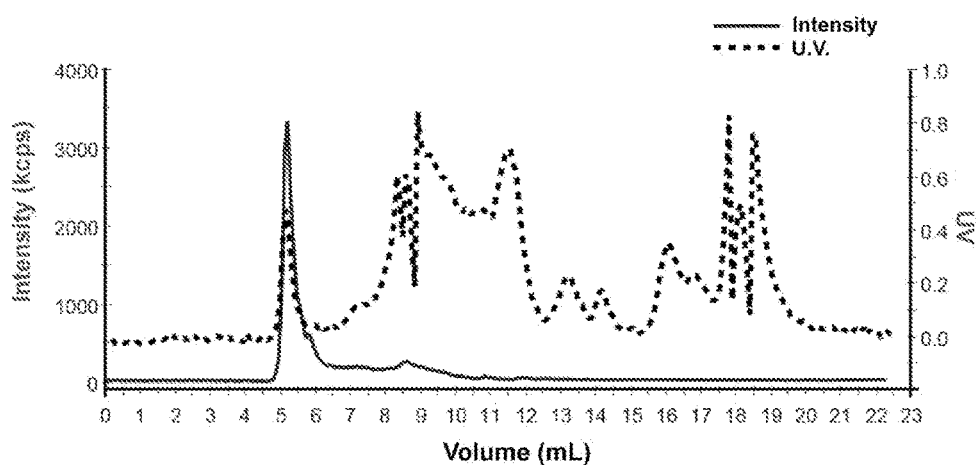
Figure 8D:
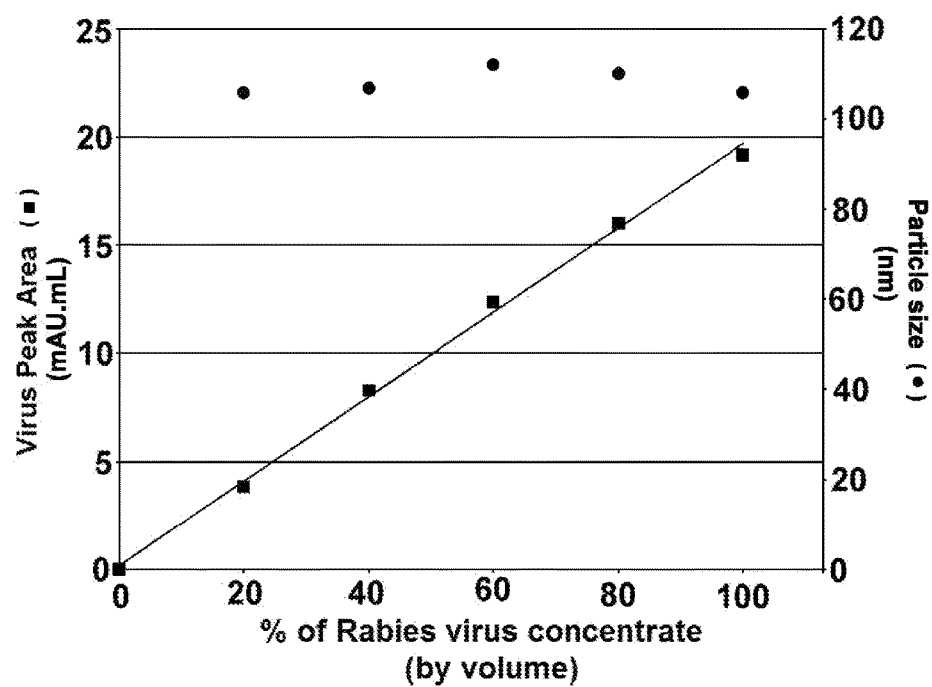
Figure 10:
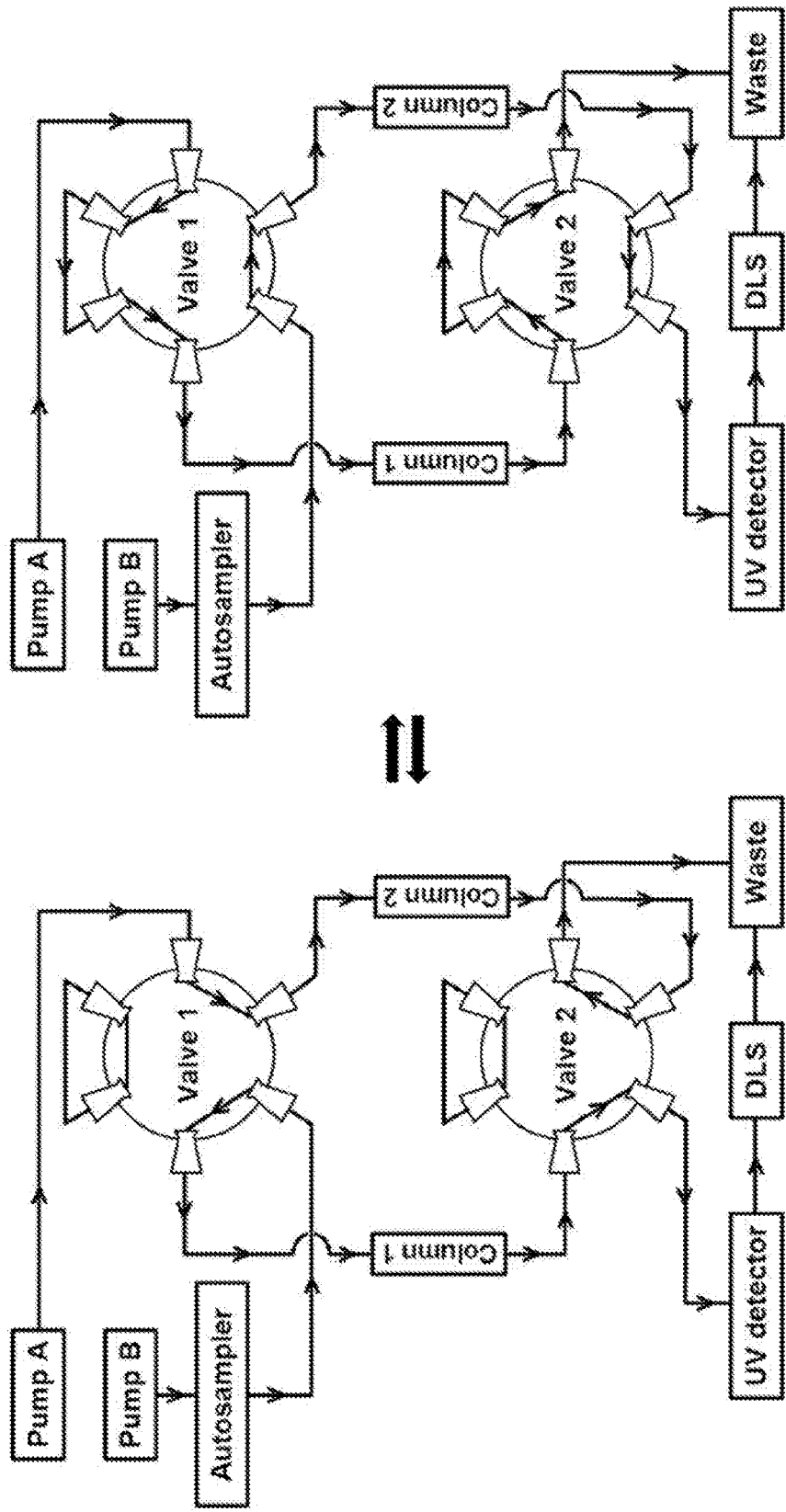

As indicated in FIG. 8D, a very high coefficient of determination $R^2$ (0.9972) was obtained showing a constant and robust association between the estimated viral concentration and the actual viral concentration of the sample, suggesting that the present invention can accurately estimate the Rabies viral particles concentration over a broad range of viral concentration.

In-line DLS particle size determinations showed constant readings ranging from 106 to 112 nm and consistent with Rabies virus particle across all the concentration range assessed (see FIG. 8D and Table 14). Indeed, the Rabies virus has a bullet shape and is described to be around 180 nm in length and 75 nm in diameter. Since the DLS detector calculates the hydrodynamic radius of each particle and since, for that purpose, the DLS considers that all the particles are spherical, it is totally logical that the size measurement obtained in this experiment ranges from 75 to 180 nm. All the results obtained from ultraviolet and DLS traces are summarized in Table 14.

TABLE 14

Ultraviolet and DLS analysis of a Rabies virus concentrate and its serial dilution samples

| % virus concentrate (by volume) | Peak area (mAU · mL) | Corrected peak area (mAU · mL) | Particle size (nm) |
|---|---|---|---|
| 0 | 0.0 | 0.0 | — |
| 20 | 3.83 | 3.83 | 106 |
| 40 | 8.28 | 8.28 | 107 |
| 60 | 12.39 | 12.39 | 112 |
| 80 | 16.03 | 16.03 | 110 |
| 100 | 19.17 | 19.17 | 106 |

Interpretation of Results

This example illustrates that the present application is capable of generating accurate measurement over a broad range of viral concentrations for enveloped viruses.

In one embodiment, this example shows that the present application is capable of generating accurate measurement for particles of enveloped viruses such as BoHV-5, PIV-3 and Rabies over a broad range of viral concentrations as indicated by the high linearity of viral concentration determined from various viral samples diluted from the viral concentrate.

This example shows the capability of the present invention to consistently and accurately characterize the size and integrity of BoHV-5 antigen, PIV-3 antigen and Rabies virus antigen independent of the viral concentration.

As demonstrated in this example, the method of the present invention is well suited to quantify and characterize enveloped viral particles in concentrated samples and therefore can be applied to ultraconcentrated BoHV-5 antigen banks or PIV-3 antigen banks or Rabies virus antigen banks.

Example 7

Monitoring FMDV Infection in Industrial Cell Culture

This example shows the use of the present invention to monitor the course of infection in a 2000 liters industrial cell culture bioreactor.

For the FMDV infection step, 2000 L of BHK (Baby Hamster Kidney) cell suspension culture in GMEM (Glasgow Minimal Essential Medium) supplemented with 12% by volume of adult bovine serum were grown to a cell concentration of 2.4×106 cell/mL. Once this cell concentration was reached, the cells were allowed to sediment and the serum-containing medium was discarded and replaced by serum-free GMEM. Once re-suspended, the cell culture was inoculated with a O1 Campos FMDV seed culture at a MOI (multiplicity of infection) ranging from 0.001 to 0.05 viable viral particles per cell. Temperature was kept constant at 37° C. before and after infection. Culture samples were withdrawn at intervals of 1 hour up to the 4th hour and every 30 minutes thereafter. Cell count was determined by microscopy counting in an Improved Neubauer hemocytometer. Remaining sample was centrifuged and the supernatant was directly analyzed using the present invention, in order to quantify the virus concentration and characterize its size and integrity. The results of Example 7 are summarized in FIG. 9 and in Table 15.

TABLE 15

Change in concentration, size and cell count of virus during the 8-hours infection

| Hours after infection | Viral concentration (μg/mL) | Particle size (nm) | Cell count ($\times 10^6$ cell/mL) |
|---|---|---|---|
| 0 | 0.03* | / | 2.38 |
| 1.0 | 0.01* | / | 2.52 |
| 2.0 | 0.01* | / | 2.56 |
| 3.0 | 0.01* | / | 2.78 |
| 4.0 | 0.12* | / | 2.80 |
| 4.5 | 0.18* | / | 2.58 |
| 5.0 | 0.19* | / | 2.54 |
| 5.5 | 0.25* | / | 2.16 |
| 6.0 | 1.22 | 31.0 | 2.06 |
| 6.5 | 2.72 | 32.3 | 1.20 |
| 7.0 | 3.85 | 33.4 | 0.60 |
| 8.0 | 5.20 | 34.7 | 0.06 |

*Those values are below the current limit of detection of the validated technique and therefore cannot be taken in this example as significantly different from the background noise.

Up to the $4^{th}$ hour after infection, cells continue to grow but no or very little virus was detected. From hour 4 to hour 6.5, virus could be detected by the U.V. detector but the signal was too low to enable an accurate DLS reading. From hour 6.5 onwards, virus was easily detectable with both U.V. and DLS detectors. The in-line DLS detector produced readings of 31-35 nm, which were fully consistent with the described diameter of FMDV.

This example shows how the quantification and the characterization technique of the present invention can perform at a very low concentration range of FMD virus particles. The U.V detector started to provide reliable readings at 254 nm at 6 hours after the beginning of the infection of the cell culture (measurement superior to 1 μg/mL, which is the current validated limit of detection (LOD)). Surprisingly, the DLS detector started to provide reliable and consistent measurement of the size of the FMDV particles at a starting concentration of 1.2 μg/mL. This represents an important feature of the present invention as the working protein concentration usually described for a normal operation of DLS detectors is in the range of 0.5 to 2 mg/mL, several orders of magnitude higher that the viral concentrations described in this example.

Also this example demonstrates that the technique of the present invention can be applied to live FMD virus particles. These data, together with the rest of the data of the present invention, further prove that the described technique can be used at absolutely every single step of manufacturing process of an FMD vaccine, no matter if the virus is still alive or if it has been already inactivated. Likewise, the technique of the present invention can be applied to every single step of manufacturing process of other types of live virus particles such as the Bovine Rotavirus, BoHV-5, PIV-3 and Rabies virus.

Finally, it can be reasonably anticipated that the use of more modern U.V. detectors, such as detectors having a bigger optical path or reduced background level, would enable to further decrease the limit of detection (LOD) and the limit of quantification (LOQ) of the present invention to, for example a LOD of 0.1 μg/mL and a LOQ of 0.3 μg/mL.

Example 8

Column-Switching System

In one embodiment, the present invention provides a method of high-throughput quantification and characterization of all enveloped and non-enveloped viruses.

Due to the nature of the size exclusion chromatography, it is usually necessary to completely elute all the peaks from the previous sample before starting a new round of chromatography for another sample. Therefore, viral antigens having a large molecular weight can be quantified during the first half of a chromatographic run, but the analysis of the next sample cannot be started until the low molecular weight components of the previous sample are completely eluted from the column. Otherwise, the virus peaks of the next sample may superimpose with the trailing peaks from the previous run sample, thereby leads to a contamination. Data captured within this time frame is useless to the purpose of quantifying virus content or determining antigen integrity. The time required to elute all the low molecular components can be regarded as unproductive idling of equipment and operator time which ultimately reduces the overall productivity of the analytical laboratory.

It is possible to increase the productivity by setting up another full HPLC system with its own pair of UV and DLS detectors but this can be very expensive and inconvenient due to space constraints in FMDV vaccine manufacturing QC laboratories. The present invention provides a column-switching system which is able to reduce the expense of having duplicated UV and DLS detectors and keep the equipment footprint at almost the same as the single column configuration.

In one embodiment, the present column-switching system is configured to include a two-valve array, two HPLC pumps, two SEC columns, one U.V. detector and one DLS detector. In another embodiment as illustrated in FIG. 10, the system further includes components such as an autosampler and a waste collector. This setup is feasible to cut the chromatography run time by half and therefore effectively doubles the productivity. It should be noted that the present column-switching system can take any suitable forms and be configured with various features and components according to the need of the quantification and characterization. For example, one may connect three HPLC pumps, three SEC columns and one DLS detector for running three batches of sample simultaneously.

As illustrated in FIG. 10, the two-valve array includes valve 1 and valve 2 which can be connected to different system components such as the pump, the autosampler, different types of columns, UV detectors and the waste collector. The two valves can be independently controlled or operated together to implement the present column-switching system.

Before running, samples to be analyzed are put into the autosampler. Appropriate buffers such as the equilibration buffer and wash buffer are put under the two pumps.

As shown in the left panel of FIG. 10, while a sample is running in Column 1 using Pump B, Column 2 is being washed and equilibrated with appropriate buffer from Pump A. After the virus peak is eluted and quantified in the UV detector and the size and integrity of the obtained virus elution is assessed in the DLS detector, the valve array is switched to the position shown in the right panel of FIG. 10.

The analysis of the next queued sample in the autosampler can then be started immediately in Column 2. Meanwhile, any low molecular weight components remaining in Column 1 that are of no interest can be flushed directly to Waste under the equilibration by Pump A. For the following samples, valve array is switched back and forth and analysis of samples eluted alternates from Column 1 and Column 2 until all samples in the autosampler are exhausted.

In one embodiment, the columns configured in the present column-switching system can be loaded with the same type of virus. In another embodiment, the columns configured in the present column-switching system can be loaded with different types of virus. In either case, the UV and DLS detectors quantify and analyze the peaks eluted sequentially from the columns to achieve a high-throughput analysis. With adequate washing of the tubing, columns and the detection system, the risk of cross-contamination is very low and therefore the accuracy of analysis is guaranteed.

In one embodiment, the valves are controlled by the same software that controls and integrates the functioning of other system components such as the pumps and autosamplers, or software that captures data from the UV and DLS detectors. In one embodiment, Agilent ChemStation Software which controls Agilent 1260 Infinity chromatograph was used to control the whole system. It is also possible to pre-set programs to implement a fully-automated process which includes but is not limited to the following steps: equilibration and washing of the column, injection of sample to the column, performing size-exclusion chromatograph with UV profile tracked, and quantification, characterization of the eluted peak using a U.V. detector and DLS detector, and waste removal from the column. Other automated or robotic system can also be used to perform steps such as the solvent (e.g. chloroform) extraction and enzymatic digestion in the pre-treatment step to further improve the efficiency of the quantification and characterization.

In one embodiment, operation of the system is tightly controlled by suitable software and system. For example, software and system that produce, integrate and analyze the UV and DLS chromatographs can be used to convert the chromatographic data of each eluted fraction to analytical data in a real-time manner for an easier interpretation. Warning systems for common error conditions (e.g. leakages, overpressure) and remote control system can also be included in the present system.

This example clearly shows that the implementation of the multi-column switching system further enhances the throughput of the analysis. The whole system demonstrates many synergistic characteristics that greatly improve the efficiency of the analysis of FMDV antigens; namely, elimination of the interference of large DNA molecules by endonuclease digestion, elimination of the interference of large lipid residues by solvent (e.g. chloroform) extraction, separation of low molecular weight molecules by SEC, elution of the virus particles in the exclusion volume (or near exclusion volume) of the SEC column, simultaneous run of two or more SEC and real-time DLS analysis. The present invention is capable of producing a pure segregated enveloped and non-enveloped virus peak and analyzing the eluted peak by the U.V. detector and the DLS detector in 20 minutes after the start of the chromatographic run. The present invention does not only achieve a high-throughput but also a more cost-effective analysis of viral antigens because the switching system does not require multiple DLS detectors and thereby minimizes the working space for setting up the whole system.

In one embodiment of the present SEC, the elution of the viral peak is completed before the 20 minutes mark after the injection of the sample for all viruses and the whole chromatography takes about 50 minutes to elute all the low and high molecular molecules from the column. Accordingly, one sample can be loaded on one column every 50 minutes for a new round separation.

In one embodiment of the present invention in which the column-switching system is implemented, analysis of the next sample can be done after the first 20-minutes analysis of the first sample and thereby maximizes the use of machinery and time. It is estimated that the present invention can complete the purification, quantification and characterization of at least 57 samples per day.

In one embodiment of the present column-switching system comprising two SEC columns, when one sample is loaded to each of the column every 50 minutes, the two columns can handle about 57 samples in every 24 hours.

In one embodiment, the present column-switching system comprises three HPLC pumps, three SEC columns, one U.V. detector and one DLS detector. Since virus peak is eluted at around 20 minutes after the sample injection, the three columns together with the U.V. and DLS detectors can handle 3 samples per hour. In this case, one sample is loaded on each of the column every 60 minutes. The two detectors recorded and analyze signals of virus eluted from the first column, and then the virus eluted from the second column and finally from the third column. After the virus peak has been eluted from the column number 3, the system switches back to column number 1 to load the next sample. Therefore, the system can handle and analyze about 72 samples in every 24 hours.

In additional to the capability of handling all types of samples from crude samples to highly purified and concentrated samples, the present invention clearly provides a very versatile, sensitive and high-throughput analysis that cannot be achieved by any current technologies such as ELISA, SRID, real-time PCR. FPLC and the 146S sucrose gradient technique.

In summary, the present invention provides methods and systems that can isolate all types of virus including enveloped, non-enveloped, DNA and RNA virus, and their antigens in high purity, quantify and characterize these products with high sensitivity and accuracy within a very short time. From the data of Examples 4-6 and FIGS. 4-9, it is undoubtedly that the present invention can be used to quantify a large diversity of viruses with high reproducibility, linearity, accuracy and sensitively independent of the viral concentration. The data present herein also proved that the present invention can determine the size and integrity of various types of viruses with high sensitivity and accuracy. More importantly, the present invention can be applied to all kind of samples; no matter it is a highly purified sample or crude samples taken from any step of the vaccine manufacturing process. The present invention can determine the quantity, size and integrity of the viral particles in a high-throughput manner without affecting the integrity of the particles. Therefore, the present invention provides analysis that truly reflects the characteristics of the viral particles as they are in the original samples. Clearly, the present invention permits a very high-throughput analysis of viral products to meet the high demand in both the quantity and quality of viral vaccines.

What is claimed is:

1. A method for measuring the quantity, size and disintegration or aggregation of one or more types of viruses or viral particles in multiple unpurified or crudely purified specimens, comprising the steps of:
    a) treating said multiple unpurified or crudely purified specimens with one or more enzymes to obtain a plurality of viral samples;
    b) setting up a chromatographic system comprising two pumps and two columns, wherein
        i. a first pump is connected to a first chromatographic column via a first valve, said first column is further connected via a second valve to a detection system comprising a Dynamic Light Scattering (DLS) detector and an UV detector; and
        ii. a second pump is connected to a second chromatographic column via said first valve, said second column is further connected via said second valve to a waste collector;
    c) applying a first viral sample to the first column, eluting the first viral sample from the first column and obtaining from said detection system data for determining the quantity, size and disintegration or aggregation of viruses or viral particles in said first viral sample, while running buffer through said second column;
    d) switching connections for said first and second pumps so that
        i. said first pump is now connected to said second column via said first valve, said second column is further connected via said second valve to said detection system; and
        ii. said second pump is now connected to said first column via said first valve, said first column is further connected via said second valve to said waste collector;
    e) applying a second viral sample to the second column, eluting said second viral sample from said second column and obtaining from said detection system data for determining the quantity, size and disintegration or aggregation of viruses or viral particles in said second viral sample, while running buffer through said first column; and
    f) repeating the steps of (c) to (e), thereby measuring the quantity, size and disintegration or aggregation of said plurality of viral samples.

2. The method of claim 1, wherein said viruses or viral particles are selected from the group consisting of enveloped viruses, non-enveloped viruses, DNA viruses, RNA viruses, live viruses, live-attenuated viruses, inactivated viruses, recombinant viruses, viral vectors, and virus-like particles.

3. The method of claim 1, wherein the viruses are selected from the group consisting of Foot and Mouth Disease viruses (FMDV), Bovine Herpesviruses 5 (BoHV-5), Bovine Herpesviruses 1 (BoHV-1), Parainfluenza 3 viruses (PIV-3), Bovine Rotaviruses, Rabies viruses, Bovine Viral Diarrhea Viruses, Bovine Respiratory Syncytial Viruses (BRSV), Porcine Circoviruses 2 (PCV-2), Porcine Reproductive and Respiratory Syndrome Viruses (PRRSV), Porcine Parvoviruses (PPV), and Bluetongue viruses (BTV).

4. The method of claim 1, wherein the first and second viral samples comprise the same or different types of viruses or viral particles.

5. The method of claim 1, wherein said unpurified or crudely purified specimens are supernatant of virus-infected cell cultures or an intermediate product from a vaccine manufacturing process.

6. The method of claim 1, wherein said one or more enzymes are endonuclease, exonuclease, restriction enzyme, DNase or RNase.

7. The method of claim 1, wherein the treatment with one or more enzymes in step (a) removes molecules interfering the quantification and characterization of said viruses.

8. The method of claim 1, wherein said unpurified or crudely purified specimens are treated with a solvent before or after treatment with said one or more enzymes in step (a).

9. The method of claim 8, wherein the solvent is a non-polar solvent selected from the group consisting of chloroform, benzene, toluene, hexane, pentane, and octane.

10. The method of claim 1, wherein the chromatographic system further comprises one or more of the following:

a) an autosampler to inject said viral samples to the chromatographic columns; and b) one or more systems to integrate and control functioning of a plurality of components of the chromatographic system.

11. The method of claim 1, wherein the data from said detection system comprises a first chromatographic profile of an eluted viral sample, wherein comparison of said first chromatographic profile with a second chromatographic profile of a reference sample of purified viruses or whole integral viral particles allows differentiation of whole integral viruses or viral particles from disintegrated viral fragments.

12. The method of claim 1, wherein the chromatographic columns are designed to separate particles with sizes in a range of 10-200 nm and molecular weights in a range of $10^5$-$10^9$ Daltons.

* * * * *